(12) United States Patent
Demers et al.

(10) Patent No.: US 9,549,662 B2
(45) Date of Patent: Jan. 24, 2017

(54) ENDOSCOPE CONNECTOR METHOD AND APPARATUS

(71) Applicant: San Marino Capital, Inc., Pasadena, CA (US)

(72) Inventors: Joseph R. Demers, Pasadena, CA (US); Marek Sekowski, Pacific Palisades, CA (US)

(73) Assignee: San Marino Capital, Inc., Pasadena, CA (US)

( * ) Notice: Subject to any disclaimer, the term of this patent is extended or adjusted under 35 U.S.C. 154(b) by 0 days.

(21) Appl. No.: 14/592,853

(22) Filed: Jan. 8, 2015

(65) Prior Publication Data

US 2015/0119644 A1 Apr. 30, 2015

Related U.S. Application Data

(62) Division of application No. 13/595,807, filed on Aug. 27, 2012, now Pat. No. 8,942,530.

(Continued)

(51) Int. Cl.
*A61B 1/00* (2006.01)
*A61B 1/06* (2006.01)
(Continued)

(52) U.S. Cl.
CPC ....... *A61B 1/00117* (2013.01); *A61B 1/00009* (2013.01); *A61B 1/0011* (2013.01);
(Continued)

(58) Field of Classification Search
CPC ......... A61B 1/00117; A61B 1/04; A61B 1/06; A61B 1/0011; A61B 1/00009; A61B 1/00144; A61B 1/0669; A61B 1/00167; A61B 1/00105; A61B 1/00124; A61B 1/00057; A61B 1/00103; A61B 1/00126; A61B 1/07; A61B 1/18; A61B 1/00186; A61B 1/0684; A61B 1/00193; G02B 6/4295; Y10T 29/49007
See application file for complete search history.

(56) References Cited

U.S. PATENT DOCUMENTS 3,261,349 A 7/1966 Wallace
3,470,876 A 10/1969 Barchilon
(Continued)

FOREIGN PATENT DOCUMENTS

DE 10 2009 021175 A1 11/2010
WO WO 00/54033 A1 9/2000
(Continued)

OTHER PUBLICATIONS

The International Search Report and The Written Opinion of the International Searching Authority for International Application No. PCT/US2012/056130 which is associated with U.S. Appl. No. 13/595,807, Mar. 7, 2013, European Patent Office.
(Continued)

*Primary Examiner* — Ryan Lepisto
(74) *Attorney, Agent, or Firm* — Pritzkau Patent Group, LLC

(57) ABSTRACT

An exemplary embodiment providing one or more improvements includes an endoscope connector for connecting any given one of a plurality of working assemblies to an imaging assembly.

10 Claims, 37 Drawing Sheets

Related U.S. Application Data

(60) Provisional application No. 61/536,644, filed on Sep. 20, 2011.

(51) Int. Cl.
*G02B 6/42* (2006.01)
*A61B 1/07* (2006.01)
*A61B 1/04* (2006.01)
*A61B 1/018* (2006.01)

(52) U.S. Cl.
CPC ...... *A61B 1/00057* (2013.01); *A61B 1/00103* (2013.01); *A61B 1/00105* (2013.01); *A61B 1/00124* (2013.01); *A61B 1/00126* (2013.01); *A61B 1/00144* (2013.01); *A61B 1/00167* (2013.01); *A61B 1/04* (2013.01); *A61B 1/06* (2013.01); *A61B 1/0669* (2013.01); *A61B 1/07* (2013.01); *G02B 6/4295* (2013.01); *A61B 1/00186* (2013.01); *A61B 1/00193* (2013.01); *A61B 1/018* (2013.01); *A61B 1/0684* (2013.01); *Y10T 29/49007* (2015.01)

(56) References Cited

U.S. PATENT DOCUMENTS

| | | |
|---|---|---|
| 3,605,725 A | 9/1971 | Bentov |
| 4,271,845 A | 6/1981 | Chikashige et al. |
| 4,327,711 A | 5/1982 | Takagi |
| 4,491,865 A | 1/1985 | Danna et al. |
| 4,573,450 A | 3/1986 | Arakawa |
| 4,586,923 A | 5/1986 | Gould et al. |
| 4,607,622 A | 8/1986 | Fritch et al. |
| 4,622,954 A | 11/1986 | Arakawa et al. |
| 4,655,219 A | 4/1987 | Petruzzi |
| 4,718,406 A | 1/1988 | Bregman et al. |
| 4,742,817 A | 5/1988 | Kawashima et al. |
| 4,745,470 A | 5/1988 | Yabe et al. |
| 4,805,595 A | 2/1989 | Kanbara |
| 4,827,909 A | 5/1989 | Kato et al. |
| 4,911,148 A | 3/1990 | Sosnowski et al. |
| 4,920,980 A | 5/1990 | Jackowski |
| 4,928,172 A | 5/1990 | Uehara et al. |
| 4,947,827 A | 8/1990 | Opie et al. |
| 5,199,417 A | 4/1993 | Muller et al. |
| 5,222,477 A | 6/1993 | Lia |
| 5,242,454 A | 9/1993 | Gundlach et al. |
| 5,284,128 A | 2/1994 | Hart |
| 5,305,121 A | 4/1994 | Moll |
| 5,307,803 A | 5/1994 | Matsuura et al. |
| 5,318,526 A | 6/1994 | Cohen |
| 5,318,528 A | 6/1994 | Heaven et al. |
| 5,361,166 A | 11/1994 | Atkinson et al. |
| 5,483,951 A | 1/1996 | Frassica et al. |
| 5,503,616 A | 4/1996 | Jones |
| 5,549,542 A | 8/1996 | Kovalcheck |
| 5,599,299 A | 2/1997 | Weaver et al. |
| 5,603,687 A * | 2/1997 | Hori ................ A61B 1/00096 348/45 |
| 5,617,498 A | 4/1997 | Cawood |
| 5,651,783 A | 7/1997 | Reynard |
| 5,700,236 A | 12/1997 | Sauer et al. |
| 5,704,892 A | 1/1998 | Adair |
| 5,704,899 A | 1/1998 | Milo |
| 5,768,461 A * | 6/1998 | Svetkoff ................ G02B 6/065 385/116 |
| 5,797,836 A | 8/1998 | Lucey et al. |
| 5,820,630 A | 10/1998 | Lind |
| 5,878,159 A | 3/1999 | Taleblou et al. |
| 5,881,195 A | 3/1999 | Walker |
| 5,895,350 A | 4/1999 | Hori |
| 5,951,463 A | 9/1999 | Lombardi et al. |
| 6,022,334 A | 2/2000 | Edwards et al. |
| 6,045,516 A | 4/2000 | Phelan |
| 6,086,528 A | 7/2000 | Adair |
| 6,091,872 A | 7/2000 | Katoot |
| 6,104,426 A | 8/2000 | Street |
| 6,129,661 A | 10/2000 | Iafrati et al. |
| 6,190,308 B1 | 2/2001 | Irion et al. |
| 6,322,498 B1 | 11/2001 | Gravenstein et al. |
| 6,332,092 B1 | 12/2001 | Deckert et al. |
| 6,428,470 B1 | 8/2002 | Thompson |
| 6,450,948 B1 | 9/2002 | Matsuura et al. |
| 6,458,076 B1 | 10/2002 | Pruitt |
| 6,487,349 B2 | 11/2002 | Wach et al. |
| 6,503,196 B1 | 1/2003 | Kehr et al. |
| 6,549,794 B1 | 4/2003 | Nadeau, Jr. et al. |
| 6,589,165 B2 | 7/2003 | Bodor et al. |
| 6,623,174 B2 | 9/2003 | Perko et al. |
| 6,654,528 B2 | 11/2003 | Rosenast |
| 6,663,560 B2 | 12/2003 | MacAulay et al. |
| 6,747,795 B2 | 6/2004 | Lin et al. |
| 6,840,909 B2 | 1/2005 | Gatto |
| 6,846,311 B2 | 1/2005 | Gatto |
| 6,863,651 B2 | 3/2005 | Remijan et al. |
| 6,882,785 B2 | 4/2005 | Eichelberger et al. |
| 6,932,762 B2 | 8/2005 | Ayame et al. |
| 6,953,430 B2 | 10/2005 | Kidooka |
| 6,991,634 B2 | 1/2006 | Sugiyama et al. |
| 7,056,284 B2 | 6/2006 | Martone et al. |
| 7,070,559 B2 | 7/2006 | Adams et al. |
| 7,292,390 B2 | 11/2007 | Lin et al. |
| 7,298,942 B2 | 11/2007 | Blasingame et al. |
| 7,404,794 B2 | 7/2008 | Scholly |
| 7,608,056 B2 | 10/2009 | Kennedy, II |
| 7,647,092 B2 | 1/2010 | Motz et al. |
| 7,708,688 B2 | 5/2010 | Welker et al. |
| 7,708,756 B2 | 5/2010 | Nobis et al. |
| 7,736,374 B2 | 6/2010 | Vaughan et al. |
| 7,758,224 B2 | 7/2010 | Hama et al. |
| 7,760,251 B2 | 7/2010 | Kuriyama |
| 7,762,948 B2 | 7/2010 | Hirata |
| 7,762,949 B2 | 7/2010 | Nakao |
| 7,764,437 B2 | 7/2010 | Yamamoto |
| 7,766,937 B2 | 8/2010 | Ravikumar |
| 7,768,641 B2 | 8/2010 | Bearman et al. |
| 7,775,972 B2 | 8/2010 | Brock et al. |
| 7,780,691 B2 | 8/2010 | Stefanchik |
| 7,785,250 B2 | 8/2010 | Nakao |
| 7,785,252 B2 | 8/2010 | Danitz et al. |
| 7,787,939 B2 | 8/2010 | Jacobsen et al. |
| 7,824,407 B2 | 11/2010 | Yamamoto et al. |
| 7,846,090 B2 | 12/2010 | Pilvisto et al. |
| 7,871,422 B2 | 1/2011 | Shibata |
| 7,901,353 B2 | 3/2011 | Vayser et al. |
| 7,918,783 B2 | 4/2011 | Maseda et al. |
| 7,942,814 B2 | 5/2011 | Remijan et al. |
| 7,951,072 B2 | 5/2011 | Adams et al. |
| 8,075,479 B2 | 12/2011 | Takahashi |
| 8,096,943 B2 | 1/2012 | Melville |
| 8,100,904 B2 | 1/2012 | Sugita et al. |
| 8,137,263 B2 | 3/2012 | Marescaux et al. |
| 8,398,540 B2 | 3/2013 | Hassidov et al. |
| 8,454,501 B2 | 6/2013 | Fernandez et al. |
| 2001/0003142 A1 | 6/2001 | Koshikawa |
| 2002/0087050 A1 | 7/2002 | Rudischhauser et al. |
| 2003/0078476 A1 | 4/2003 | Hill |
| 2003/0142753 A1 | 7/2003 | Gunday |
| 2003/0174208 A1 | 9/2003 | Glukhovsky et al. |
| 2005/0254720 A1 | 11/2005 | Tan et al. |
| 2005/0278010 A1 | 12/2005 | Richardson |
| 2006/0045444 A1 * | 3/2006 | Miller ................ C03C 25/107 385/115 |
| 2009/0240143 A1 | 9/2009 | Osdoit et al. |
| 2009/0326321 A1 | 12/2009 | Jacobsen et al. |
| 2011/0054252 A1 | 3/2011 | Ozaki et al. |
| 2011/0123154 A1 | 5/2011 | Eberle et al. |
| 2011/0213300 A1 | 9/2011 | McWeeney et al. |

FOREIGN PATENT DOCUMENTS

| | | |
|---|---|---|
| WO | WO 00/54653 A1 | 9/2000 |
| WO | WO 01/19235 | 3/2001 |

(56) References Cited

FOREIGN PATENT DOCUMENTS

| WO | WO 2006/122303 A2 | 11/2006 |
|---|---|---|
| WO | WO 2008/112312 | 9/2008 |
| WO | WO 2010/071816 A1 | 6/2010 |

OTHER PUBLICATIONS

W. Al Sarakbi, Does Mammary Ductoscopy Have a Role in Clinical Practice?, Mar. 10, 2006, International Seminars in Surgical Oncology, vol. 3, 2006.
International Preliminary Report on Patentability and Written Opinion of the International Searching Authority for International Application No. PCT/US2012/056130 which is associated with U.S. Appl. No. 13/595,807, Mar. 25, 2014, The International Bureau of WIPO, Geneva, Switzerland.
Manjiyu et al., Translation of JP 2001161629 A, Jun. 19, 2001.

* cited by examiner

ENDOSCOPE CONNECTOR METHOD AND APPARATUS

RELATED APPLICATION

The present application is a divisional of U.S. patent application Ser. No. 13/595,807, filed on Aug. 27, 2012 which itself claims priority from U.S. Provisional Patent Application Ser. No. 61/536,644, filed on Sep. 20, 2011, each of which applications are hereby incorporated by reference in their entireties.

BACKGROUND

Endoscopes have continued to evolve since their inception in the 1800's because of their utility and versatility. Medical endoscopes can be used for performing medical procedures which can include viewing and manipulating tissues in body cavities. While relatively large endoscope probes can be used in existing body channels for some types of procedures, other relatively small endoscope probes can be used to perform intricate surgery through relatively small incisions. Because of these relatively small incisions, patient recovery time and surgical complications can be significantly reduced when compared to similar procedures using non-endoscopic techniques.

A conventional endoscope can have a probe with a distal end for insertion through an incision into a body cavity. The probe can be rigid or flexible and can include one or more channels that extend from the distal end to a proximal end. The probe can include an imaging fiber bundle that is used in conjunction with a viewing apparatus for viewing objects in a field of view in the body cavity. The probe can also include one or more illumination fibers arranged to transfer light from an illumination source to illuminate the field of view, and can include a working channel for guiding tools through the probe into the body cavity for performing surgical techniques.

A challenge in medical endoscopes is economical manufacturing and utilization. A typical medical endoscope can cost thousands of dollars. Historically, surgical endoscopes have been relatively expensive and have been sterilized and reused to avoid the cost of having to replace the instrument after every procedure. Sterilization and reuse can be economical and safe for endoscopes having relatively large probes. On the other hand, Applicants submit that effective and economical sterilization techniques have not been realized for a clinical setting for endoscopes having smaller channels that are on the order of 1 mm or less. Because of this, some smaller endoscopes are disposed of following surgery which can increase the cost of the procedure.

Applicants recognize that endoscopy costs can be significantly decreased if the working assembly of the endoscope can be removed from the imaging assembly. The working assembly can be disposable and can have as short an imaging fiber as practical, which can help decrease unit cost for the disposable working assembly. In order to achieve this however, it can be necessary to have a connector which connects the disposable, single-use working assembly to the imaging assembly through which images may be transferred. While methods of connection exist, they are typically bulky and do not lend themselves to quick connection, such as by snapping into place, nor are they small and light. Applicants recognize that useful connector embodiments include features such as, for example: a small size in order to allow it, along with the working assembly of the endoscope, to be easily held and manipulated by the practitioner; and extremely tight positional accuracy after thousands of connections. None of these useful embodiments are believed to be available with conventional endoscope devices.

The present invention provides a highly advantageous system and method that are submitted to resolve the foregoing problems and concerns while providing still further advantages, as described hereinafter.

SUMMARY OF THE INVENTION

An imaging fiber connector arrangement is disclosed for optically coupling a working assembly including an imaging fiber bundle having a plurality of imaging fiber cores to an imaging assembly. An imaging assembly connector fitting forms part of the imaging assembly and has an optical assembly that includes an active optical element. The optical assembly is configured to receive and modify images before passing the images to the imaging assembly. The optical assembly has a focal plane that is essentially at a distal surface of the active optical element. A working assembly connector fitting forms part of the working assembly and is configured to engage the imaging assembly connector fitting to removably optically couple the imaging fiber bundle of the working assembly to the imaging assembly. The imaging assembly connector fitting and working assembly connector fitting are configured to position a proximal end of the imaging fiber cores of the imaging fiber bundle in a predetermined location in three dimensions relative to the active optical element. The predetermined location is within the focal plane of the active optical element, to within a given tolerance such that images are coupled from the imaging fiber bundle directly to the active optical element without passing through any intervening inactive optical element when the working assembly connector fitting is engaged with the imaging assembly connector fitting.

An imaging fiber connector arrangement is disclosed which form part of a working assembly and part of an imaging assembly for optically coupling a working assembly, including a working assembly imaging fiber bundle having a plurality of imaging fiber cores to the imaging assembly. The working assembly fiber cores are arranged to receive images at a distal end from a field of view and to transmit the images to proximal ends of the working assembly fiber cores. An imaging assembly connector fitting is included, which forms part of the imaging assembly and includes an optical assembly having an active optical element. The active optical element is supported in the imaging assembly connector fitting at least in part to receive images from the proximal end of the working assembly fiber cores and to perform a predetermined optical function on the images. The optical assembly defines a focal plane that is at least essentially at a distal surface of the active optical element as supported in the imaging assembly connector fitting. A working assembly connector fitting forms part of the working assembly and is configured to engage the imaging assembly connector fitting to removably optically couple the imaging fiber bundle of the working assembly to the imaging assembly by indexing the proximal ends of said imaging fiber cores of the imaging fiber bundle to a predetermined position in three dimensions to establish a specific tolerance with respect to the active optical element. Images emitted from the imaging fiber bundle couple directly to the active optical element without passing through any intervening inactive optical element when the working assembly connector fitting is engaged with the imaging assembly connector fitting. The predetermined position is characterized by an axial distance between the proximal ends of the imaging fiber cores within a limited range from the distal surface of the active optical element as part of said specific tolerance.

An imaging fiber connector arrangement is disclosed which forms part of a working assembly and part of an imaging assembly for optically coupling the working assembly, including an working assembly imaging fiber bundle having a plurality of imaging fiber cores, to the imaging assembly. The working assembly fiber cores are arranged to receive images at a distal end from a field of view and to transmit the images to proximal ends of the working assembly fiber cores. An imaging assembly connector fitting forms part of the imaging assembly and has a plurality of light receiving elements, the light receiving elements are configured to receive images. A working assembly connector fitting forms part of the working assembly and is configured to engage the imaging assembly connector fitting to removably optically couple the working assembly imaging fiber bundle to the light receiving elements of the imaging assembly connector fitting by positioning the proximal end of the working assembly fiber cores in a predetermined location in three dimensions relative to the light receiving elements to within a specific tolerance such that images from the working assembly fiber cores optically couple to the light receiving elements when the working assembly connector fitting is engaged with the imaging assembly connector fitting.

An endoscope working assembly is disclosed which includes an imaging fiber bundle having a plurality of fiber cores. The fiber cores are arranged to receive images at a distal end from a field of view and to transmit the images to a proximal end of the fiber cores and emit the images from the proximal end. An electronic imaging sensor includes multiple individual light sensing pixels and is configured to produce electrical video signals in response to receiving images. The imaging sensor optically is coupled to the imaging fiber bundle to receive the images from the proximal end of the fiber cores such that images from each fiber core are received by at least one of the light sensing pixels. A working assembly connector fitting is connected to the imaging fiber bundle and the electronic imaging sensor and is configured to engage an imaging assembly connector fitting of an imaging assembly to removably attach the working assembly to the imaging assembly and is arranged to electrically communicate the electrical video signals from the electronic imaging sensor to the imaging assembly.

An imaging fiber connector arrangement is disclosed which forms part of a working assembly and part of an imaging assembly for optically coupling the working assembly to the imaging assembly. An imaging assembly connector fitting forms part of the imaging arrangement and has an optical assembly configured to receive images for the imaging assembly. The optical assembly includes an imaging assembly optical element having a distal surface through which the images are initially received. The imaging assembly connector fitting defines an alignment bore. A working assembly connector fitting forms part of the working assembly and is configured to engage the imaging assembly connector fitting to removably optically couple a working assembly imaging fiber bundle to the imaging assembly. The working assembly connector fitting including a ferrule which supports a proximal end of working assembly fiber cores of the working assembly imaging fiber bundle. The ferrule and the working assembly fiber core ends have a polished end configuration that operates as an active optical element. The ferrule is configured to engage the alignment bore when the working assembly connector fitting engages the imaging assembly connector fitting to index the polished end relative to the distal surface of the imaging assembly optical element such that the polished end cooperates with the optical assembly to perform a predetermined optical function in addition to guiding the images from the working assembly imaging fiber bundle to the imaging assembly without substantial optical loss.

An endoscope is disclosed which includes a working assembly including a working assembly imaging fiber bundle having a plurality of working assembly fiber cores. The working assembly fiber cores are arranged to receive images at a distal end from a field of view and to transmit the images to a proximal end of the working assembly fiber cores and emit the images from the proximal end of the working assembly fiber cores. The images from each working assembly fiber core have an image amplitude and at least one other image characteristic. An imaging assembly includes an imaging assembly imaging fiber bundle having a plurality of imaging assembly fiber cores arranged to receive the images at a distal end and to transmit the images to a proximal end of the imaging assembly fiber cores and emit the images from the proximal end of the imaging assembly fiber cores. The imaging assembly includes an imaging processor arranged to receive the images from the proximal end of the imaging assembly fiber cores and to extract the image characteristic from the image to produce image information based on the image characteristic for use by the imaging assembly. An imaging fiber connector arrangement includes an imaging assembly connector fitting attached to the imaging assembly imaging fiber bundle and a working assembly connector fitting attached to the working assembly imaging fiber bundle. The imaging fiber connector arrangement is configured to engage the imaging assembly connector fitting to removably optically couple the working assembly to the imaging assembly and to transfer the images with the image characteristic from each of the working assembly fiber cores to a plurality of the imaging assembly fiber cores.

An endoscope is disclosed which includes a working assembly including a working assembly imaging fiber bundle having a plurality of imaging fiber cores. The working assembly fiber cores are arranged to receive images at a distal end from a field of view and to transmit the images to a proximal end of the working assembly fiber cores and emit the images from the proximal end of the working assembly fiber cores. The working assembly includes a plurality of illumination fibers each having a distal end adjacent to the distal end of the working assembly fiber cores and spatially separated from one another at the distal ends. A plurality of illumination sources are configured to provide light for insertion into proximal ends of the illumination fibers to transmit the light to the distal ends of the illumination fibers for illumination of the field of view. An imaging assembly includes an imaging processor that is configured to receive the images from the working assembly fiber cores and to control at least two of the illumination sources to sequentially illuminate the viewing area to produce at least two images of the field of view that contain different characteristics. The imaging processor is further configured to utilize the different characteristics to produce a synthetic stereoscope image responsive to said spatial separation.

An endoscope is disclosed that includes optics which introduces at least one image distortion characteristic to images produced by the endoscope. A working assembly includes a distal end arranged to produce images of a field of view of the working assembly. The working assembly includes a working assembly connector fitting. A packaging arrangement is removably attached to the working assembly.

The packaging arrangement has a predetermined picture in the field of view of the working assembly when attached to the working assembly. An imaging assembly includes an imaging assembly connector fitting that is configured to engage the working assembly connector fitting to removably optically couple the working assembly to the imaging assembly to transfer a predetermined picture image of the predetermined picture which includes the distortion characteristic from the working assembly to the imaging assembly. The imaging assembly includes a calibration arrangement to receive the distorted predetermined picture image from the working assembly. The calibration arrangement includes a predetermined image standard based on the predetermined picture. The calibration arrangement compares the distorted predetermined picture image to the predetermined image standard to produce a calibration mask that can be applied to images from the field of view to compensate for the distortion characteristic in the images.

A calibration arrangement is disclosed for calibrating an endoscope that includes optics which introduces at least one image distortion characteristic to images. The endoscope includes an imaging assembly and a working assembly having a distal end arranged to produce images of a field of view of the working assembly. The working assembly includes a working assembly connector fitting. The imaging assembly includes an imaging assembly connector fitting that is configured to engage the working assembly connector fitting to removably optically couple the working assembly to the imaging assembly to transfer images from the working assembly to the imaging assembly. The calibration arrangement includes a packaging arrangement for removably attaching to the working assembly. The packaging arrangement has a predetermined picture in the field of view of the working assembly when the packaging arrangement is attached to the working assembly. The calibration arrangement also includes a calibration arrangement which controls the imaging assembly to produce a predetermined picture image of the predetermined picture. The predetermined picture image includes the distortion characteristic. The calibration arrangement includes a predetermined image standard based on the predetermined picture. The calibration arrangement receives the distorted predetermined picture image from the working assembly and compares the distorted predetermined picture image to the predetermined image standard to produce a calibration mask that can be applied to images from the field of view to compensate for the distortion characteristic in the images.

A method for calibrating an endoscope having a working assembly and an imaging assembly is disclosed. The endoscope includes optics which introduces at least one image distortion characteristic to images produced by the endoscope. A packaging arrangement is removably attached to a working assembly to impose a predetermined picture into a field of view of the working assembly. The predetermined picture is imaged to produce a distorted predetermined picture image that includes the distortion characteristic. The distorted predetermined picture image is compared to a predetermined image standard to produce a calibration mask, based at least in part on differences between the distorted predetermined picture image and the predetermined image standard. The calibration mask can be applied to images from the field of view to compensate for the distortion characteristic in the images.

BRIEF DESCRIPTION OF THE DRAWINGS

The present invention is illustrated by way of example in the following drawings wherein such like references indicate similar elements. The following drawings disclose various embodiments of the present invention for purposes of illustration only and are not intended to limit the scope of the invention.

DETAILED DESCRIPTION OF THE INVENTION

Figure 1:
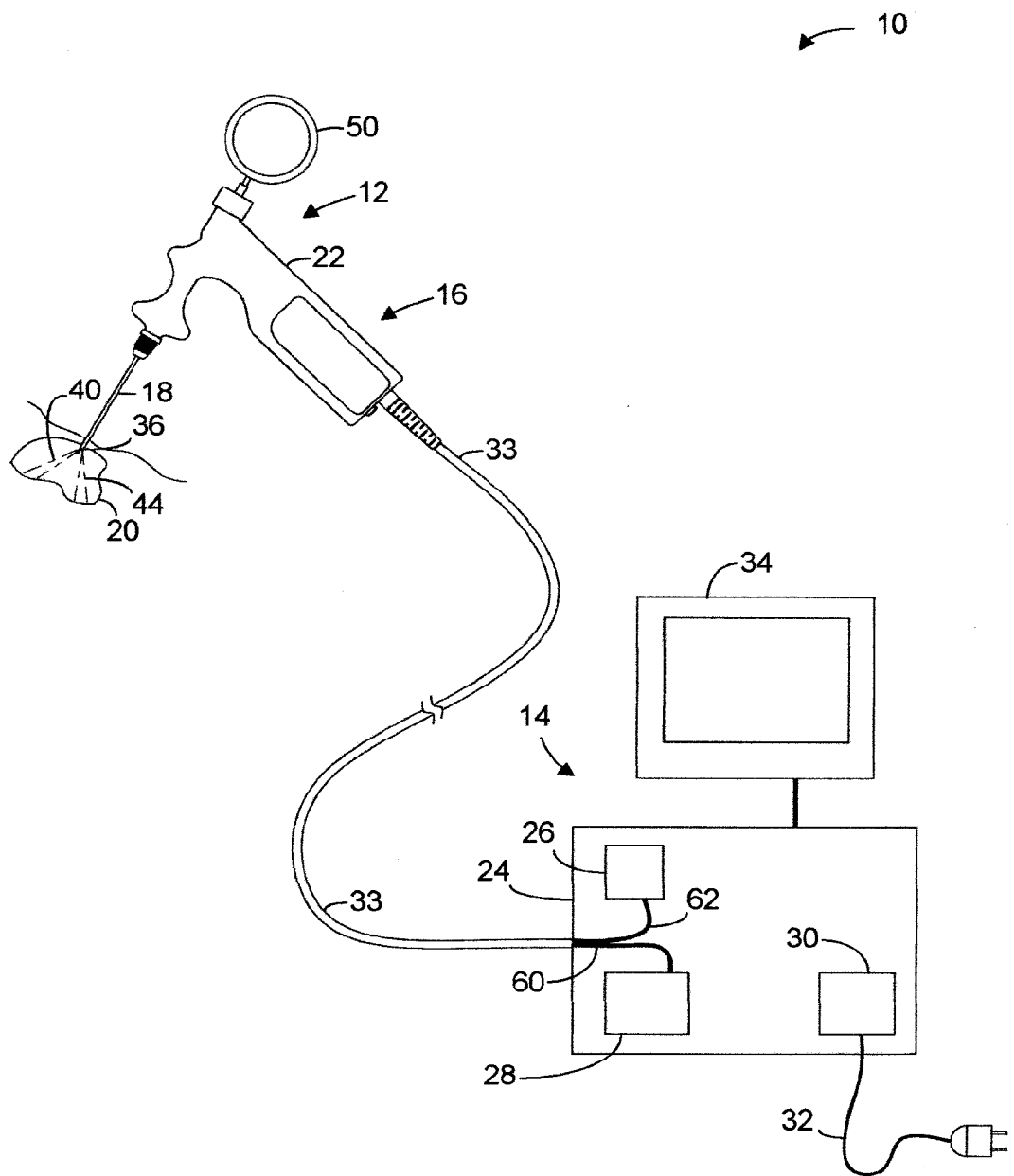
FIG. 1 is a diagrammatic illustration of an embodiment of an endoscope.

While this invention is susceptible to embodiment in many different forms, there are shown in the drawings, and will be described herein in detail, specific embodiments thereof with the understanding that the present disclosure is to be considered as demonstrating principles of the invention and is not to be limited to the specific embodiments described. Descriptive terminology may be adopted for purposes of enhancing the reader's understanding, with respect to the various views provided in the figures, and is in no way intended to be limiting.

Referring to the drawings, wherein like components may be indicated by like reference numbers throughout the various figures, FIG. 1 illustrates an embodiment of an endoscope 10, having a working assembly 12 and an imaging assembly 14 which can be removably connected to one another using a connector 16. The working assembly can include a probe 18 for insertion into a body cavity 20 for performing a surgical procedure which can include viewing into the body cavity and manipulating tissue. The probe is attached to a handle body 22 which can be grasped by a person to manipulate the probe.

The imaging assembly can have an imaging assembly housing 24 which can include an illumination source 26, an imaging processor 28, and a power supply 30 which can receive power through a power cable 32 from a common power source and which can provide power to the endoscope. The imaging assembly can also include a viewing device 34 for viewing images created by the endoscope. The imaging assembly can be connected to the working assembly with a cable 33.

Figure 2:
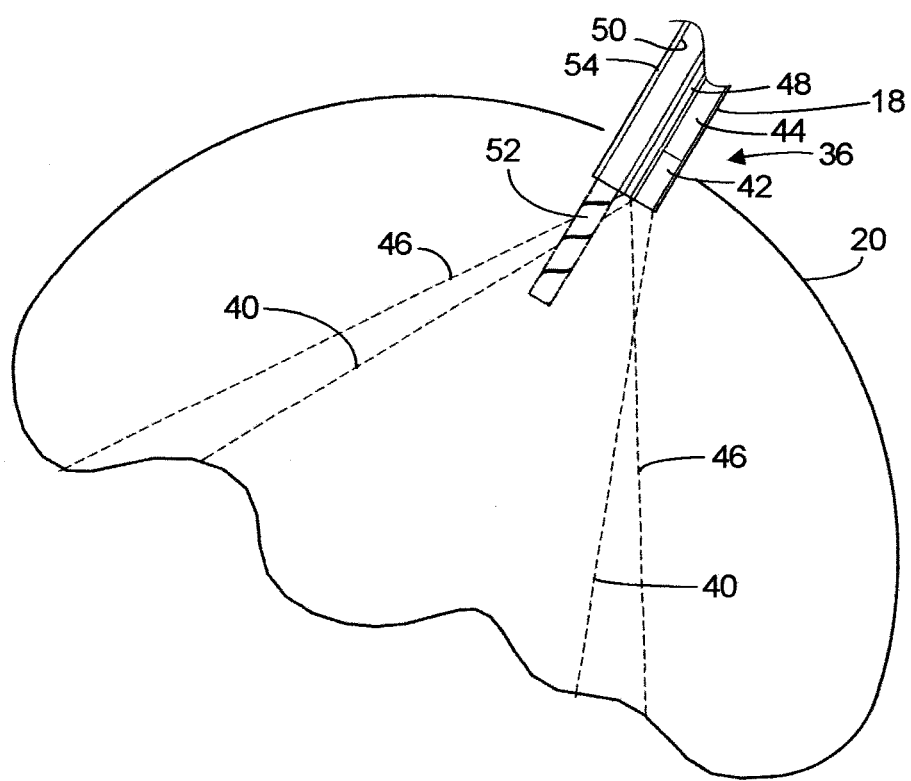
FIG. 2 is a diagrammatic cut away illustration of a distal end of a working assembly of the endoscope shown in FIG. 1.

Turning now to FIG. 2 in conjunction with FIG. 1, a distal end 36 of probe 18 can be used for imaging a field of view of an objective lens 38 as represented by dashed lines 40. The objective lens can be optically coupled to a distal end 42 of an imaging fiber bundle 44 which carries the image to the connector in the handle body. The illumination source can generate light, represented by dashed lines 46, which can be transferred to the distal end of the probe at least partially with an illumination fiber 48. The light can be used for illuminating at least a portion of the body cavity that is in the field of view of the objective lens. The probe can also include a working channel 50 for guiding a tool 52 from the handle body to the body cavity. The probe can include a sheath 54 that defines the working channel and which contains the imaging fiber bundle and illumination fiber. The probe can be rigid or flexible and can be manufactured with different lengths.

Figure 3:
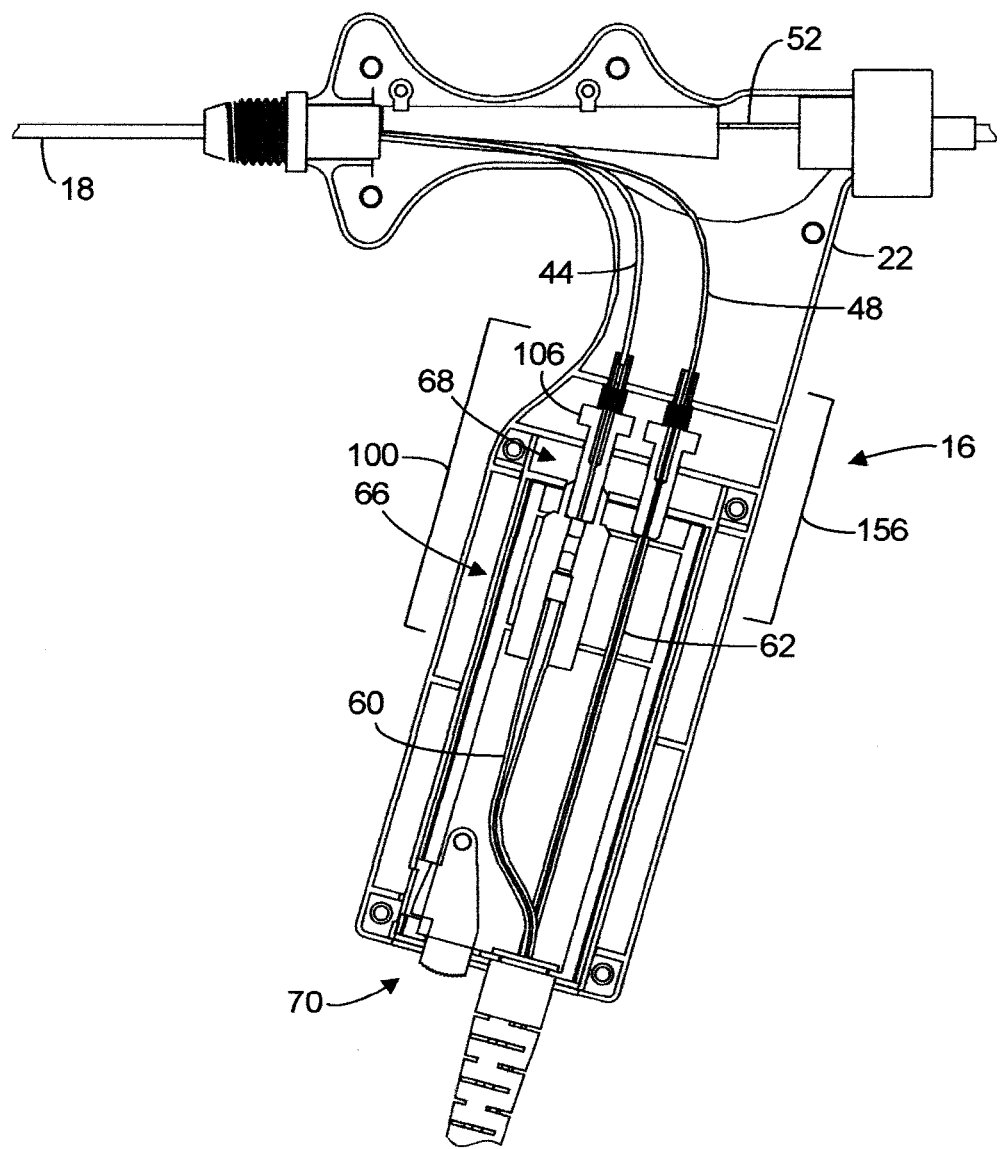
FIG. 3 is a diagrammatic cut away illustration of a connector of the endoscope of FIG. 1.

Referring now to FIG. 3, an enlarged, partially cut away view of connector 16 is presented. Distal imaging lens 38 images a portion of the body cavity in the field of view of the objective lens and image light from the field of view is guided through imaging fiber bundle 44 to connector 16. The imaging fiber can be a permanent part of the working assembly, as shown in FIGS. 1-3, or can be installed and removed via a working channel in the working assembly. The connector, in an embodiment, optically couples imaging fiber bundle 44 to an imaging fiber bundle 60 of cable 33 of the imaging assembly which then guides the image light to imaging processor 28. The imaging processor can include a lens eyepiece and/or imaging electronics. The imaging processor can convert or otherwise transform the image light to a format which can be utilized to gain information about the image, such as transforming the image light into a format that can readily be viewed by a person using viewing device 34. The connector can also optically couple an illumination fiber 62 of cable 33 of the imaging assembly, which is connected to illumination source 26, to illumination fiber 48 of the working assembly to transfer the light from the illumination source to the distal end of the probe.

Connector 16 can include an imaging assembly connector fitting 66 and a working assembly connector fitting 68 which are configured for removable engagement of the working assembly and the imaging assembly for purposes of optically coupling imaging light and/or illumination light between the working and imaging assemblies. A latching mechanism 70 can be included for latching the connector fittings together. Multiple working assemblies can be manufactured with working assembly connector fittings that are essentially identical so that any given one of the working assemblies can be connected to and used with the imaging assembly. The components making up the imaging assembly can be considerably more expensive than the components making up the working assembly. The working assemblies can be made relatively inexpensively in comparison to the imaging assembly, so that it is not cost prohibitive to dispose of the working assembly after a single use while re-using the imaging assembly with multiple working assemblies over a long period of time. This can be advantageous since effective and economical sterilization techniques are not believed to have not been realized in a clinical setting for endoscopes having smaller channels that are on the order of 1 mm or less. The working assembly can be economically manufactured and sterilized during the manufacturing process. Following a surgical procedure, the working assembly can be disconnected from the imaging assembly and can be disposed. The relatively more expensive and larger diameter imaging fiber bundle for the imaging assembly can be re-used with the imaging assembly. This relatively larger diameter imaging fiber bundle can also more suitable for use with the imaging assembly rather than with the working assembly since larger core imaging fibers can be very stiff and difficult to bend.

Figure 4:
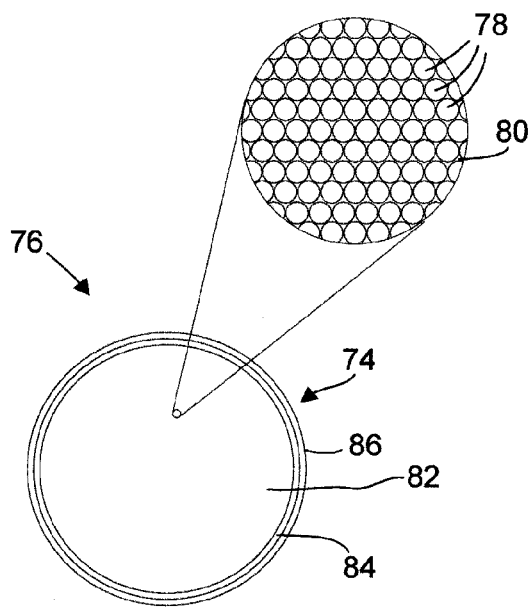
FIG. 4 is a diagrammatic illustration of an imaging fiber end.

Referring now to FIG. 4, an end face 74 of an imaging fiber bundle 76 is shown. Imaging fiber bundle 76 is a diagrammatic illustration of a typical imaging fiber bundle and is shown as an example of component parts that may be found in working assembly imaging fiber bundle 44 and/or imaging assembly imaging fiber bundle 60. Imaging fiber bundle 76 can be constructed with multiple individual fiber cores 78 that are surrounded individually and collectively by a common cladding 80. The end face of the imaging fiber bundle with the fiber cores and the cladding can be collectively referred to as an image circle 82 which can be surrounded by a jacketing 84, that can be made from silica, and which can be covered by a plastic coating 86. The individual fiber cores of the bundle may also be referred to as elements of the imaging fiber bundle and the end areas of the fiber cores can serve as pixels. Imaging fiber bundles can be made to have a diameter that is less than 1 millimeter and can have several thousand fiber cores. The element size and density of the imaging fiber cores can determine the pixel size for the transmitted image and the flexibility of the imaging fiber bundle. For example, an imaging fiber bundle can have ten thousand 3.5 micrometer diameter fiber cores and can have an outer diameter of 0.35 mm.

While imaging fiber bundles can be formed in many different diameters and with various element quantities, the maximum element density remains roughly the same for the various diameters. This is due at least partially to the nature of transmitting white light along a fiber and minimizing color dispersion. Smaller individual fibers required for higher element density would increase the fiber density, but the fibers would have greater loss at longer wavelengths. Smaller individual fibers can also be significantly more difficult to manufacture. As a comparison to the fiber bundle with 10,000 fiber cores, a fiber bundle having ten times the number of fiber cores (100,000) has a correspondingly larger bundle diameter of approximately 1.5 mm. The fiber diameters of the larger fiber bundle can also be slightly larger at about 4.7 micrometers.

Figure 5:
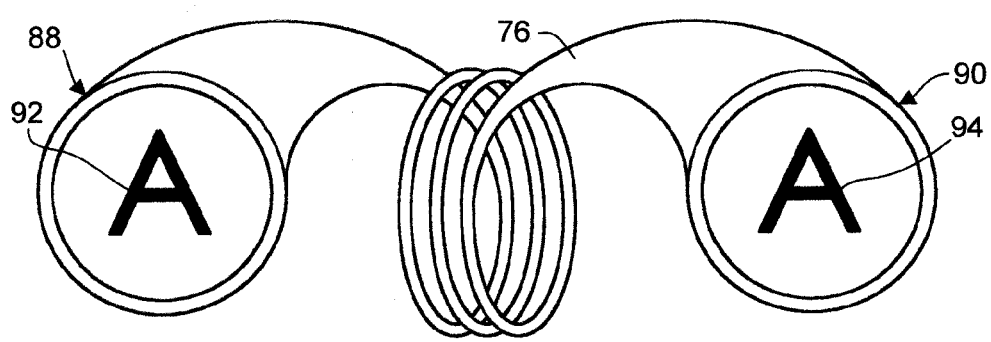
FIG. 5 is a diagrammatic illustration of a spatially consistent imaging fiber.

Referring now to FIG. 5 in conjunction with FIG. 4, during use, each of the fiber cores of imaging fiber bundle 76 can act as a pixel of the image produced by the image circle and each fiber core can transmit a pixel of the image via internal reflection of the image light between a first end 88 and a second end 90, unless the fiber core is damaged. The imaging fiber can be spatially consistent with itself, meaning that there is a one to one correspondence between the position of the elements on the input end of the bundle as compared to the output end of the bundle, as illustrated by image 92 at the first end and image 94 at the second end of image fiber bundle 76. This makes it possible to transmit an image along the bundle. If the elements were not spatially consistent, and had elements that changed their relative positions along the length of the imaging fiber bundle, then an image transmitted through the bundle would exit the bundle with the spatial information distorted (i.e. a different image would be formed).

Figure 6:
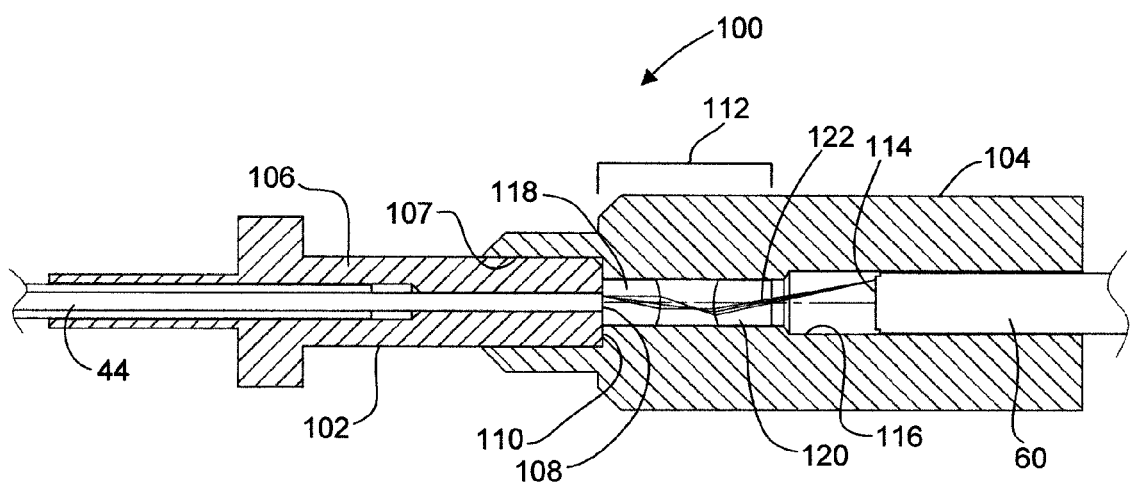
FIG. 6 is a diagrammatic cut away illustration of an embodiment of a portion of the connector.

Referring now to FIG. 6 in conjunction with FIG. 3, an imaging fiber portion 100 of connector 16 is diagrammatically shown. Imaging fiber portion 100 can include a working side fitting 102 of working assembly connector fitting 68 and imaging side fitting 104 of imaging assembly connector fitting 66. In an embodiment, imaging fiber bundle 44 of the working assembly is positioned in and connected to a ferrule 106 of working assembly connector fitting 68 and imaging side fitting 104 includes a bore 107 that is sized to receive ferrule 106.

A proximal end 108 of imaging fiber bundle 44 can be polished to be flat and co-planar with an end face 110 of ferrule 102, or to have other shapes as is discussed below. Imaging assembly connector fitting 66 can include an optical assembly 112 that can optically couple image light, represented by ray traces 122, from proximal end 108 of the working assembly imaging fiber to a distal end 114 of imaging assembly imaging fiber 60. Imaging assembly imaging fiber bundle 60 can have more fiber cores and a larger image circle diameter than the imaging fiber bundle of the working assembly. Imaging assembly connector fitting 66 can have a bore 116 within which fiber bundle 60 can be secured such that distal end 114 of fiber bundle 60 is facing toward optical assembly 112 in a confronting relationship therewith.

Optical assembly 112 can include an active optical element 118 and a secondary optics 120. Including the optical assembly in the imaging assembly connector fitting can be economically advantageous because the imaging assembly connector fitting can be reused and therefore does not add to the cost of the disposable, single-use working assembly portion of the endoscope. In another embodiment, the optical assembly can be included in the working assembly connector fitting. In any case, the optical assembly can be configured to image proximal end 108 of imaging fiber bundle 44 and to optically couple the image to distal end 114 of imaging assembly fiber bundle 60, as represented by ray traces 122. The optical assembly can magnify the image from proximal end 108 to distal end 114, for example the optical assembly can have a magnification factor in a range of one to ten.

Optical assembly 112 can be configured to image from an individual fiber core of imaging fiber bundle 44 to at least one fiber core of imaging assembly fiber bundle 60. In an embodiment, the optical assembly can be configured to image from each individual fiber core of imaging fiber bundle 44 to multiple fiber cores of imaging assembly fiber bundle 60; in one example of this configuration, the imaging assembly fiber bundle can have more fiber cores than the imaging fiber bundle of the working assembly. The imaging assembly fiber bundle can have more fiber cores than the imaging fiber bundle of the working assembly when the imaging assembly fiber bundle has a larger image circle diameter than the working assembly fiber bundle, or if the imaging assembly fiber bundle has a higher fiber core density than the working assembly fiber bundle. A magnification ratio of at least one element of the working assembly imaging fiber to one imaging assembly imaging fiber element can result in an optical coupling behavior similar to that of butt coupling the two imaging fibers together. The higher the ratio of the imaging assembly fiber cores to working assembly fiber cores, the more the working assembly imaging fiber will serve as a limit to the system resolution.

As an example embodiment, the working assembly fiber bundle can have 10,000 fiber cores and can be optically coupled to a 50,000 fiber core imaging assembly fiber bundle using magnification provided by optical assembly 112. In this arrangement, the image from the working assembly fiber bundle can be magnified by a factor of 3.2 times to fill the image circle of the imaging assembly fiber bundle. This is effectively a factor of five increase in the element density of the imaging assembly fiber bundle relative to the working assembly fiber bundle and at least approximately five elements on the imaging assembly fiber bundle are utilized to image a single element on the working assembly fiber bundle. An effective density of the imaging assembly imaging fiber can be increased through the use of magnification to magnify the image between the proximal end of the working assembly fiber bundle and the distal end of the imaging fiber imaging bundle.

Figure 7:
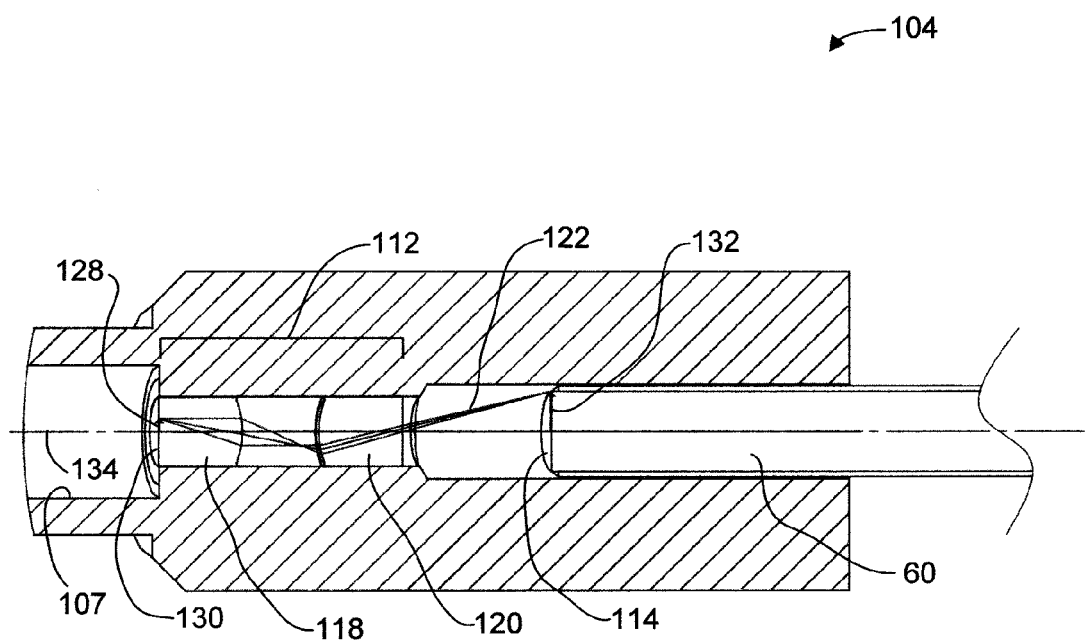
FIG. 7 is a diagrammatic cut away illustration of a portion of the connector shown in FIG. 6.

Referring now to FIG. 7 in conjunction with FIG. 6, active optical element 118 and secondary optics 120 can cooperate to focus and magnify the image of each working assembly fiber core pixel at proximal end 108 of the working assembly fiber bundle cores. The secondary optics can be chosen to set the magnification. Optical assembly 112 can have a distal focal plane represented by arrow 128 that is co-planar with a distal surface 130 of active optical element 118. The optical assembly can have a proximal focal plane represented by arrow 132 that is co-planar with distal end 114 of imaging assembly fiber bundle 60. The active optical element can serve as an environmental seal to prevent contamination between the active optical element and the secondary optics.

Imaging assembly connector fitting 66 and working assembly connector fitting 68 can be configured such that when fittings 66 and 68 engage and connect to one another, the fiber cores at proximal end 108 of working assembly fiber bundle 44 are in physical contact with distal surface 130 of active optical element 118. With the working assembly fiber bundle cores in physical contact against the distal surface of the active optical element, the fiber cores at proximal end 108 are at focal plane 128 of optical assembly 112, which serves to transfer the images from the working assembly fiber bundle cores to the imaging assembly fiber bundle cores. While the focal plane of the optical assembly may not be exactly at the distal surface of the active optical element, the focal plane can be essentially at the distal surface of the active optical element within a very short distance, such as on the order of less than one micron.

In an embodiment, the focal plane of the optical assembly can be a very short distance from the distal surface of the active optical element, such as in a range of from 10 microns to 1 millimeter, however in these circumstances the proximal end of the working assembly fiber bundle cores should be placed as close as possible to the focal plane and any gap between the distal surface of the active optical element and the working assembly fiber bundle cores can be filled with an index matching gel. A gap between the distal surface of the active optical element and the working assembly fiber bundle cores may be attributed to manufacturing tolerances.

In order to reduce the size of the imaging assembly connector fitting, the length of the optical assembly can be as short as possible. The distance between active optical element 118 and secondary optics 120 can be directly related to the position of distal focal plane 128. A minimal distance between active optical element 118 and secondary optics 120 can position the focal plane at distal surface 130 of the active optical element. Moving the distal focal plane of the optical assembly away from the distal surface of the active optical element can require increasing the distance between the active optical element and the secondary optics, thereby increasing the length of the optical assembly. Accordingly, in order to reduce the length of the optical assembly the focal plane can be as close as possible or co-planar with the distal surface of the active optical element. To image the proximal ends of the working assembly fiber cores, the fiber core ends are positioned at the focal plane of the optical assembly which precludes the use of any intervening non-active optical element, such as a window, between the fiber core ends and the distal surface of the active optical element to minimize the length of the optical assembly. Any non-active optical element, which is not involved in modifying the images, between the distal surface of the active optical element and the fiber core ends of the working assembly imaging fiber bundle can increase the overall length of the optical assembly.

Referring to FIG. 6, the proximal ends of the working assembly fiber cores can be positioned at the distal focal plane of the optical assembly within a given tolerance that is sub-micron because this first element is active and of very short focal length. In the embodiment shown in FIG. 6, end face 110 of ferrule 106 is co-planar with the proximal ends of the working assembly fiber core ends and distal focal plane 128 is co-planar with distal surface 130 of the active optical element. When working assembly connector fitting 68 is engaged with imaging assembly connector fitting 66 (FIG. 3), ferrule 106 of working side fitting 102 is positionally aligned in three dimensions in bore 107 of imaging side fitting 104 (FIGS. 6 and 7) to optically couple imaging fiber 44 to imaging fiber 60. Ferrule 106 can position the proximal end of imaging fiber bundle 44 on a common longitudinal axis 134 of optical assembly 112 and imaging fiber bundle 60. Ferrule 106 has an exterior diameter and bore 107 has an interior diameter such that ferrule 106 fits engages bore 107 within a given tolerance, which can be less than one micron, to position imaging fiber bundle 44 in two-dimensions normal to the common center axis to within the specific tolerance. The working assembly imaging fiber bundle can be positioned to within the specific tolerance in a third dimension along the common center axis by positioning proximal end 108 of the working assembly imaging fiber cores in physical contact against the distal surface of the active optical element thereby positioning the proximal end of the working assembly imaging fiber cores at distal focal plane 128 of the optical assembly.

The imaging assembly connector fitting can be used with numerous different working assembly connector fittings of numerous different disposable working assemblies. The useful lifetime of the connector can depend on how long the connection remains accurate after extensive repeated use. Therefore at least the imaging assembly connector fitting can be formed from a material that is hard and resists wear to prolong the useful lifetime of the connector. The connector fittings can be made from metal, such as stainless steel or other metals, and/or ceramic and may also be made from one or more suitable types of plastic.

There are certain types of optical connectors that are used in fiber optic communication applications which can be utilized for working side fitting 102 of working assembly connector fitting 68 in some embodiments. These communication connector fittings are typically used for transferring optical power between two single element fibers and come in several different standard configurations for use in different applications in the communications industry, such as for example LC, SC, FC and SMA to name a few. These fittings have ferrules that are formed with different inner and outer diameters and can be purchased inexpensively since they are produced in high volume for the communications industry. For example, it is possible to purchase a standard fiber optics connector which has an internal ceramic or metal ferrule having an I.D. of anywhere from 230 um to 1580 um. Standard fiber diameters (with coating stripped away) can vary from 210 um to 1500 um and can therefore be easily inserted into a connector fitting with a corresponding I.D. One of the aspects of employing an LC, SC, FC or SMA connector is that a significant amount of work has already gone into developing a connector that will align the center of the ferrules with sub-micron tolerances, which can be extremely important in regards to constructing a connector for essentially distortion free transfer of an image.

In some embodiments the optical assembly can be designed to transfer an image without inducing any significant undesired chromatic or spatial aberration. In other embodiments the optical assembly can be designed to correct chromatic and spatial aberrations imposed by objective lens 38 (FIG. 2) or other sources in the working assembly. Calibration for chromatic and spatial aberrations can be performed given a calibrated starting point for the image and image processing. A technique that is heretofore unseen by Applicants is brought to light below.

Figure 8:
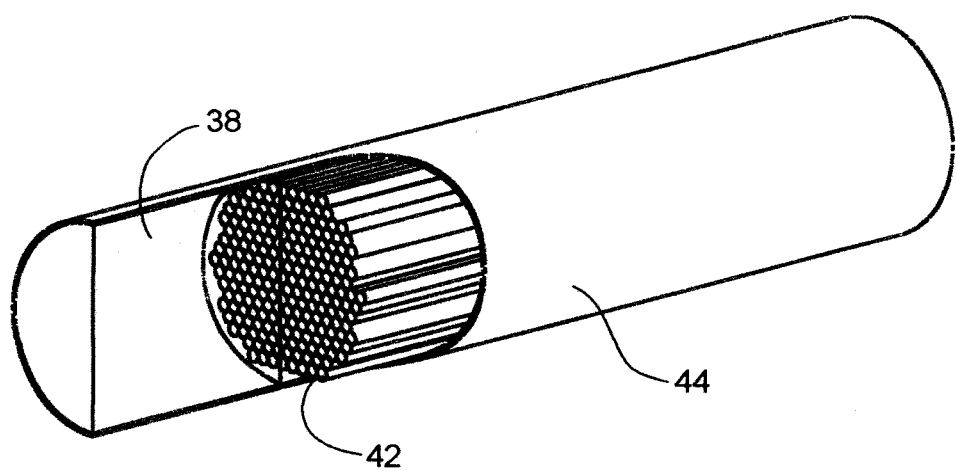
FIG. 8 is a diagrammatic cut away perspective illustration of an embodiment of a distal end of an imaging fiber.
Figure 9:
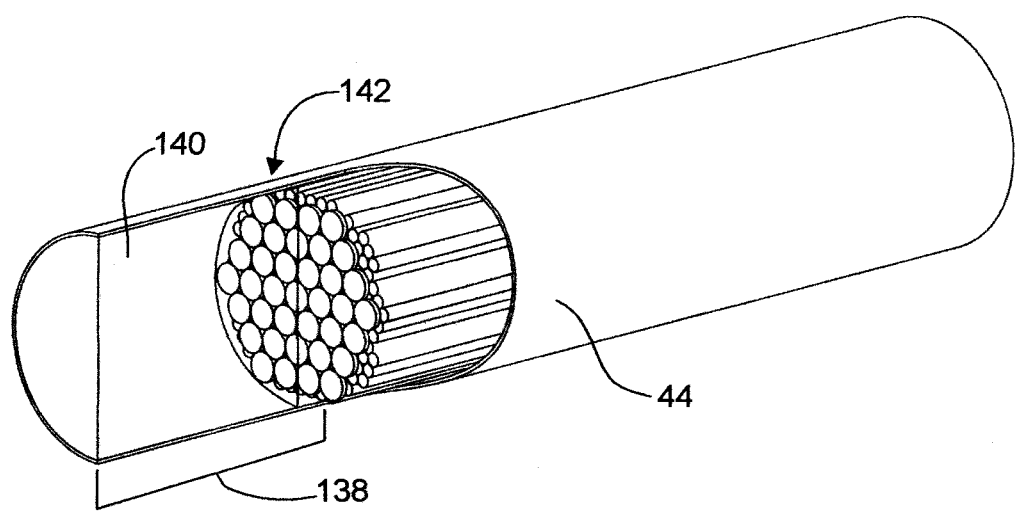
FIG. 9 is a diagrammatic cut away perspective illustration of another embodiment of a distal end of an imaging fiber.

Referring now to FIG. 8 in conjunction with FIGS. 1 and 2, distal imaging lens 38 can also be referred to as an objective lens. By way of non-limiting example, the lens can be a gradient index optics (commonly abbreviated as GRIN) lens due the economical nature of GRIN lenses and the ease with which the lens can be attached to distal end 42 of imaging fiber bundle 44. The imaging lens can be aligned with the imaging fiber cores of imaging fiber bundle 44 in a channel defined by sheath 54 (FIG. 2). It is recognized, however, that there are higher quality, and more expensive, lens systems available such as aspheres, doublets and combinations of both which can limit the amount of chromatic and spherical aberrations that would occur and thus limit the need for image correction in the connector or with image processing. Accordingly, any suitable lens can be used to achieve a desired level of optical performance. The optical assembly and/or image processing can be designed to handle images from a lens system 138 which can include a GRIN lens 140 and a multiple lens array 142, such as is shown in FIG. 9, and which can be employed for 3D imaging.

Figure 10:
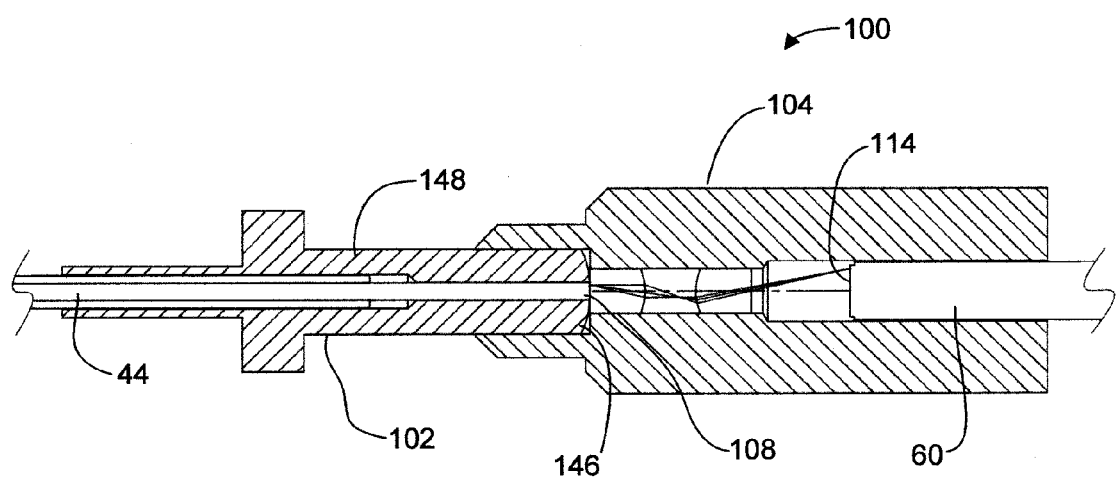
FIG. 10 is a diagrammatic cut away illustration of another embodiment of a portion of a connector.

Referring now to FIG. 10, the proximal end 108 of the fiber cores of working assembly imaging fiber bundle 44 can have a rounded end polish configuration 146 that can serve as an active optical element, for example a lens, for use in magnifying the image. The fiber core ends can be positioned in a ferrule 148. Ferrule 148 and fiber core ends 108 can be polished together to form rounded end polish configuration 146. In another embodiment, the proximal end of the fiber cores of the working assembly imaging fiber bundle can an aspherical end polish configuration which may exhibit less aberration. Based on the descriptions of the embodiments brought to light herein it should be apparent that other suitable end polish configurations can be used.

Figure 11:
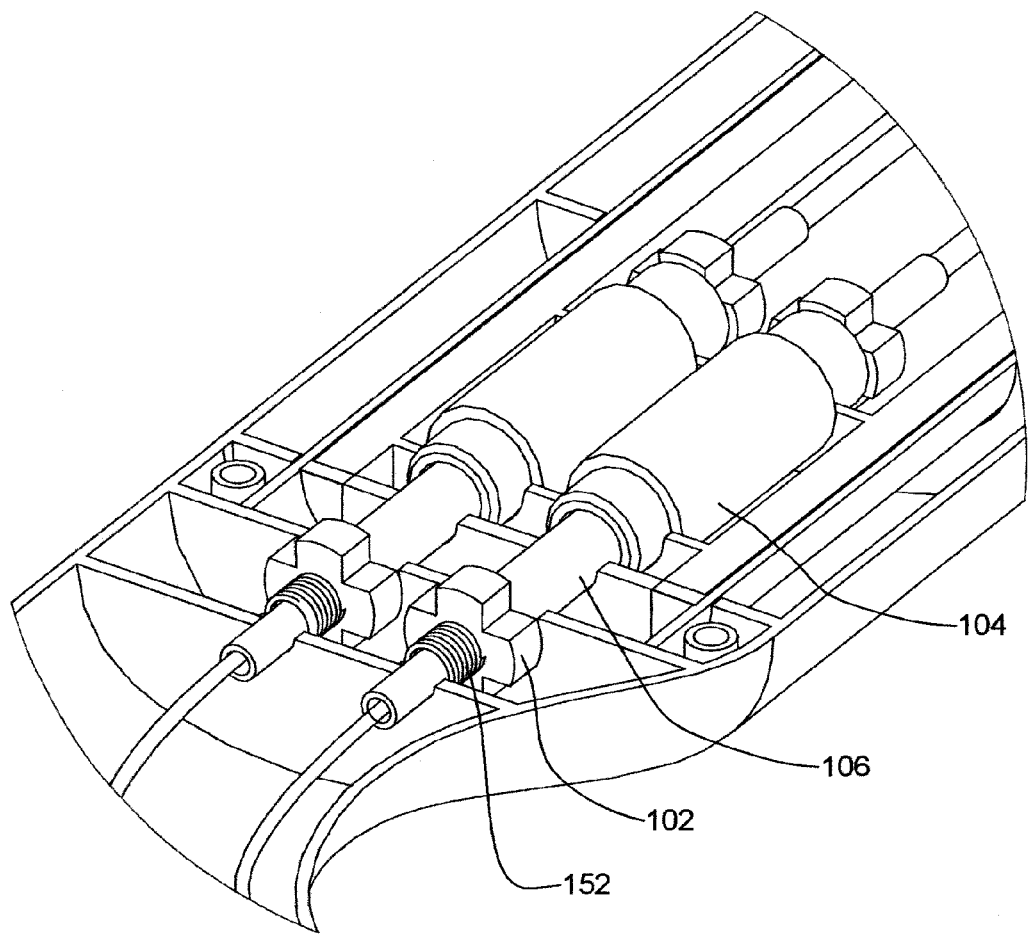
FIG. 11 is a diagrammatic partial cut away perspective illustration of another embodiment of a portion of a connector.

Referring now to FIG. 11 in conjunction with FIG. 3, connector 16 can include a bias spring 152 which can be arranged to resiliently bias the ferrule and the attached ends of the fiber cores of the working assembly imaging fiber bundle against the active optical element of the optical assembly. The bias spring can be configured to maintain the fiber core ends against the active optical element to position the fiber core ends in an axial direction.

Figure 12:
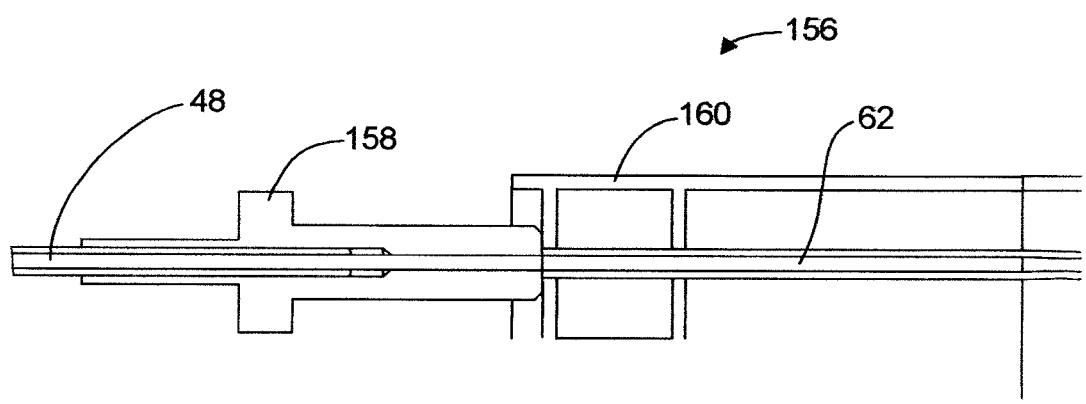
FIG. 12 is a diagrammatic cut away illustration of another embodiment of another portion of a connector.

Referring now to FIG. 12 in conjunction with FIG. 3, connector 16 can include an illumination fiber connector portion 156 having a working side fitting 158 and an imaging side fitting 160. The connector can optically couple illumination fiber 62 of the imaging assembly, which is connected to illumination source 26 (FIG. 1), to illumination fiber 48 of the working assembly to transfer the light from the illumination source to the distal end of probe 18. In an embodiment, working side fitting 158 can be a standard optical connector, which can butt-couple illumination fiber 62 to illumination fiber 62 to optically couple the illumination fibers.

Figure 13:
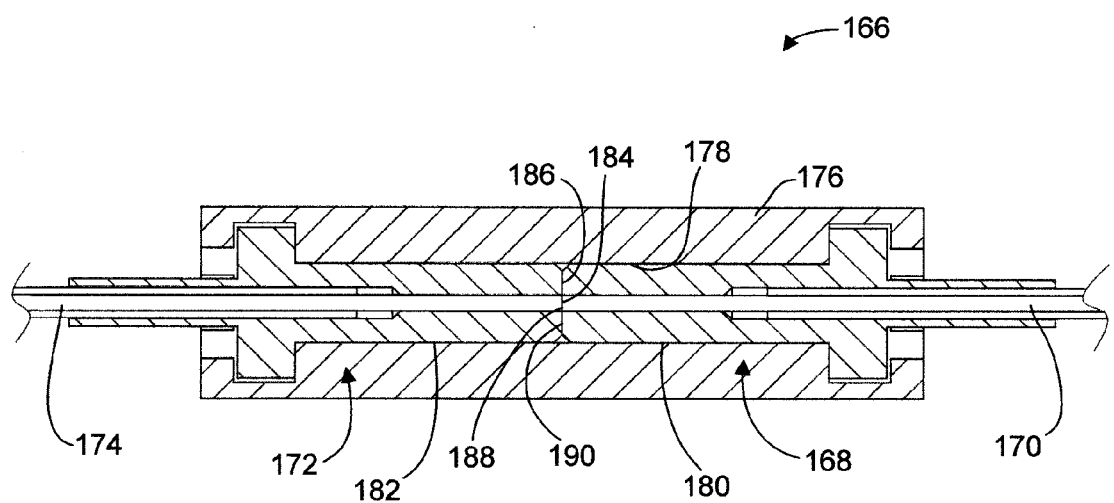
FIG. 13 is a diagrammatic cut away illustration of another connector.

Referring now to FIG. 13, a diagrammatic representation of a butt-coupled imaging fiber connector 166 is shown. Connector 166 includes an imaging assembly connector fitting 168 that is attached to an imaging assembly imaging fiber bundle 170; and a working assembly connector fitting 172 that is attached to a working assembly imaging fiber bundle 174. Connector 166 also includes a sleeve 176 that defines a bore 178 for aligning a ferrule 180 of the imaging assembly connector fitting with a ferrule 182 of the working assembly connector fitting in two dimensions. A proximal end 184 of the working assembly imaging fiber cores can be polished co-planar with an end face 186 of ferrule 182 while a distal end 188 of the imaging assembly imaging fiber cores can be polished co-planar with an end face 190 of ferrule 180. Ferrules 180 and 182 can be inserted into opposite ends of bore 178 until end face 186 contacts end face 190, which aligns the working assembly imaging fiber bundle to the imaging assembly imaging fiber bundle in two dimensions while contact between the two end faces aligns the fibers in a third dimension along a common center axis.

Figure 14:
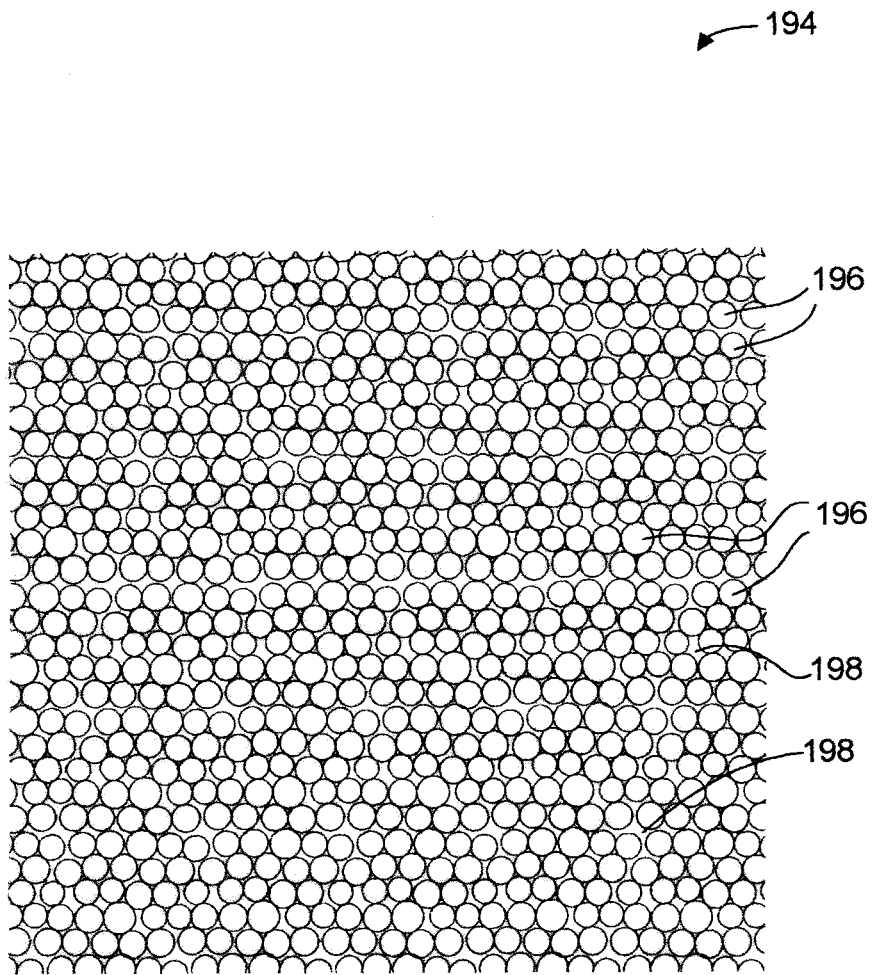
FIG. 14 is an image of an end of a portion of an imaging fiber.

As illustrated by a diagrammatic, further enlarged, representation of an end view of a portion of a typical imaging fiber bundle 194, shown in FIG. 14, fiber cores 196 are not arranged according to a fixed pattern and are fairly random in a common cladding 198 as to where the centers of the individual fibers are positioned. While the typical image fiber bundle is spatially consistent with itself, the elements in the bundle do not typically follow a specific pattern and the centers of the individual elements can be inconsistent in their position relative to each other. The shape and size of the elements can also vary and the positioning of the elements varies from one imaging fiber to another. The image through the imaging fiber bundle can have a "chicken wire" effect in that the image includes a relatively dark pattern that looks similar to chicken wire caused by the common cladding separating the individual imaging fibers. A second chicken wire pattern can be created by a fiber-to-fiber-connector and can potentially overlay the first chicken wire pattern; however Applicants have discovered that the second pattern can disappear if the magnification is sufficiently high, such as, for example a magnification of 3 greater.

Figure 15:
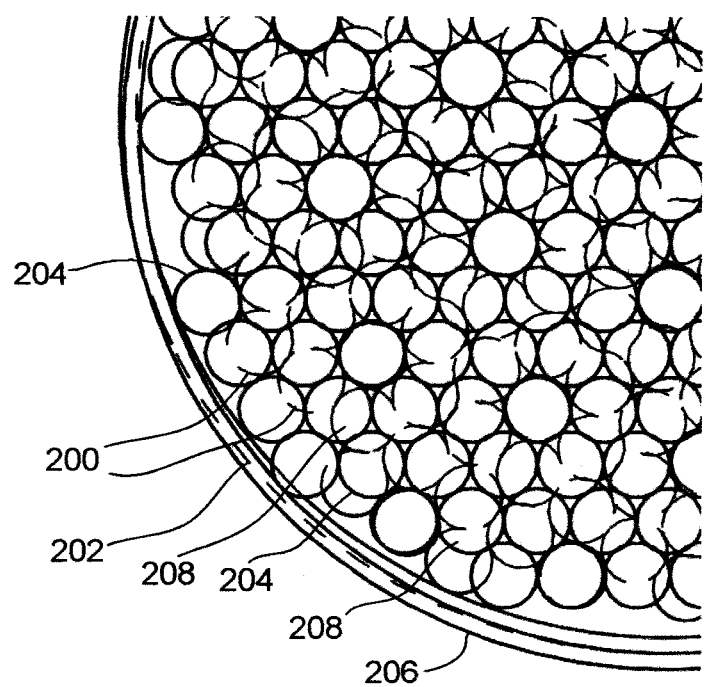
FIG. 15 is a diagrammatic illustration of ends of two imaging fibers.

Simple butt-coupling can be an approach to optically coupling the proximal end of the working assembly imaging fiber to the distal end of the imaging assembly imaging fiber in which the two imaging fibers are similar in size and density and the ends of the imaging fibers are positioned in contact with one another. However, the previously described spatial variation between fiber cores can make transferring the image via a simple butt-coupled connection difficult. Even if care is taken to align the imaging fibers well, it is extremely unlikely that anything reasonably approaching perfect alignment can be achieved and more likely there will be lateral and rotational misalignment of the elements between the fiber bundles. FIG. 15 is an illustration representing elements 200 (shown with dashed lines) of a proximal end of an imaging fiber bundle 202 and elements 204 (shown with solid lines) of a distal end of another imaging fiber bundle 206. As shown, even if some of the elements of the two imaging fibers are aligned, other elements are not aligned, as shown by partially overlapped areas 208. If the elements of the two fiber bundles do not line up directly, much of the image light is not transferred and the resulting image is similar to an image created using a decreased number of fiber cores. When the elements of the two fiber bundles are not directly lined up, image light output from several elements in the distal fiber bundle can combine into several elements in the proximal fiber bundle and can also be lost in the cladding between the fiber cores of the proximal fiber bundle. Variances in fiber core shape and center position from one fiber bundle to the other can make butt-coupled optical transfer even more complex.

Figure 16:
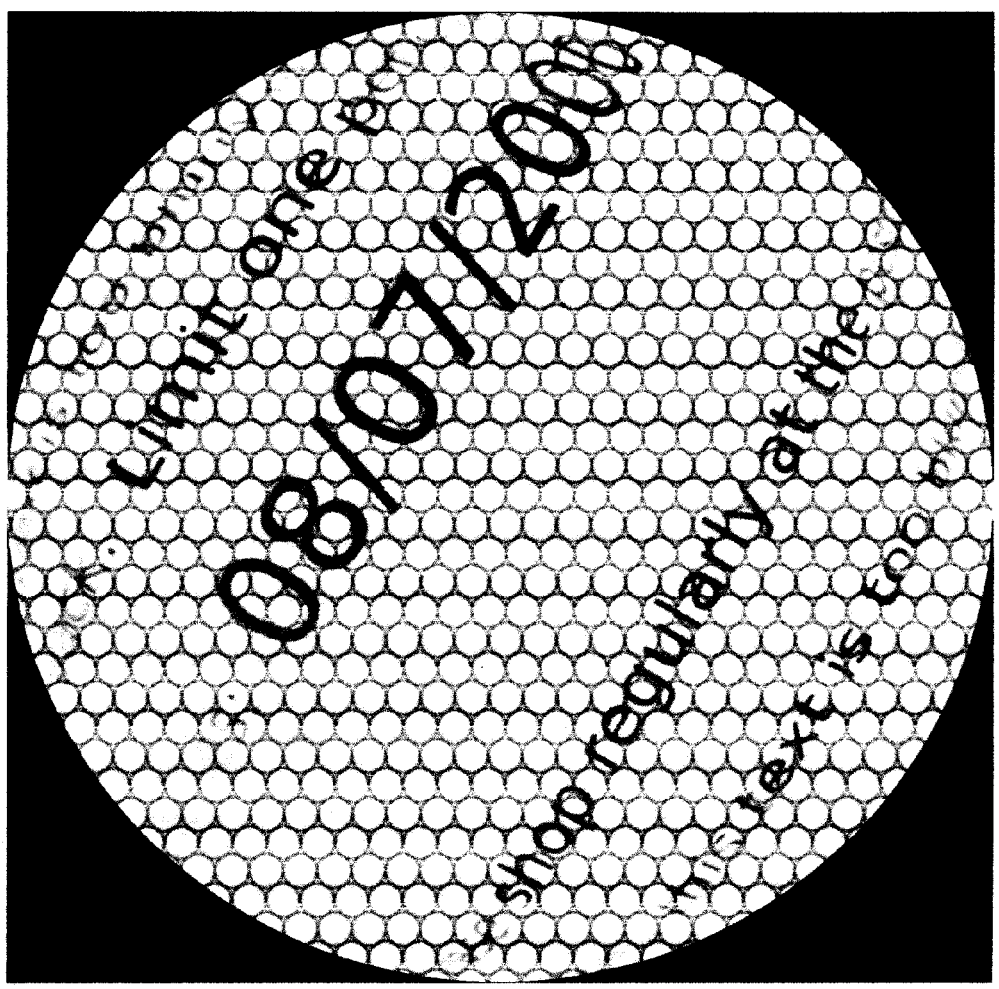
FIG. 16 is a picture representing an image seen through an imaging fiber without a connector.
Figure 17:
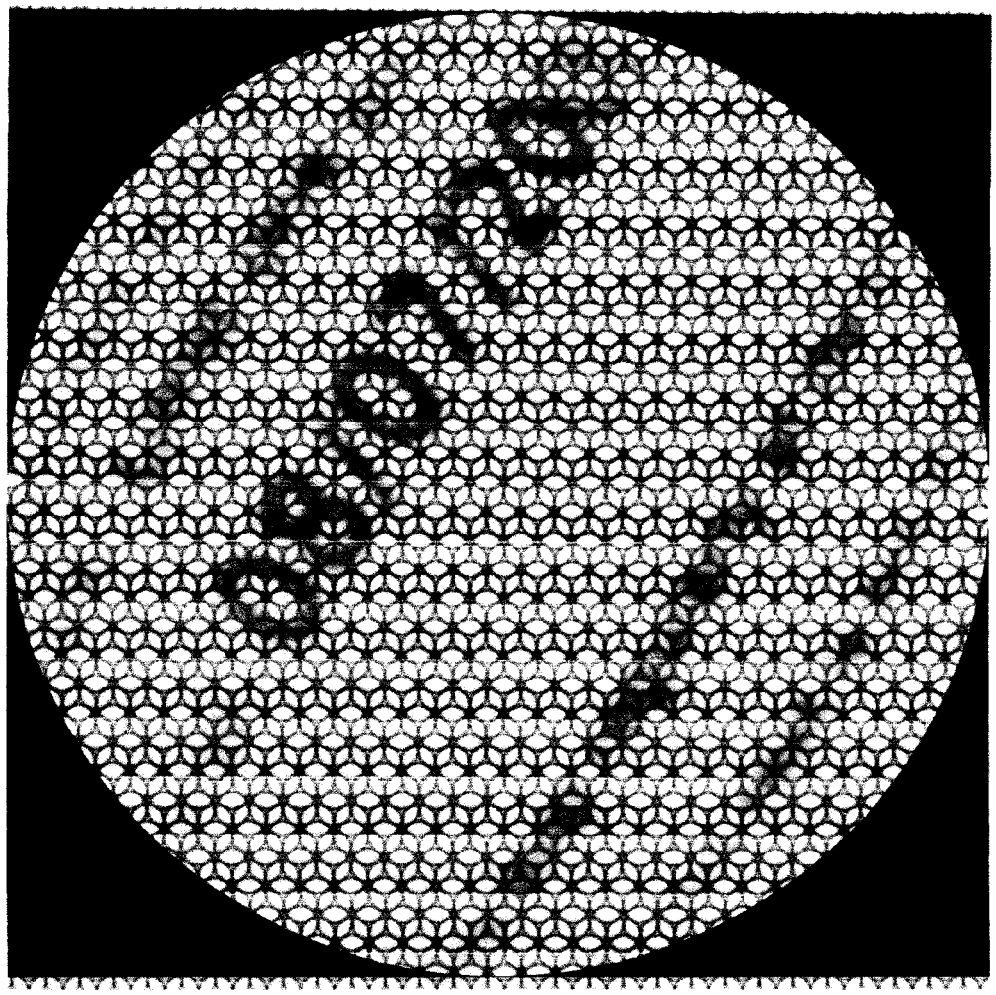
FIG. 17 is a picture representing an image seen through an imaging fiber with a butt-couple connection.

FIG. 16 illustrates an image 210 that is transmitted along an imaging fiber without a butt-coupled interface and FIG. 17 illustrates an image 212 that has been transmitted along the same imaging fiber shown in FIG. 16 except that the imaging fiber used in FIG. 17 was interfaced through simple butt-coupling. FIG. 17 demonstrates the effect of some light in the butt coupling falling onto the gaps between fiber cores at the end of the receiving fiber in the butt coupling interface on the distal section. The effect on the image can be to blur the image which can be caused by combining the partial output from several fibers into more fibers as illustrated by FIG. 15.

Figure 18:
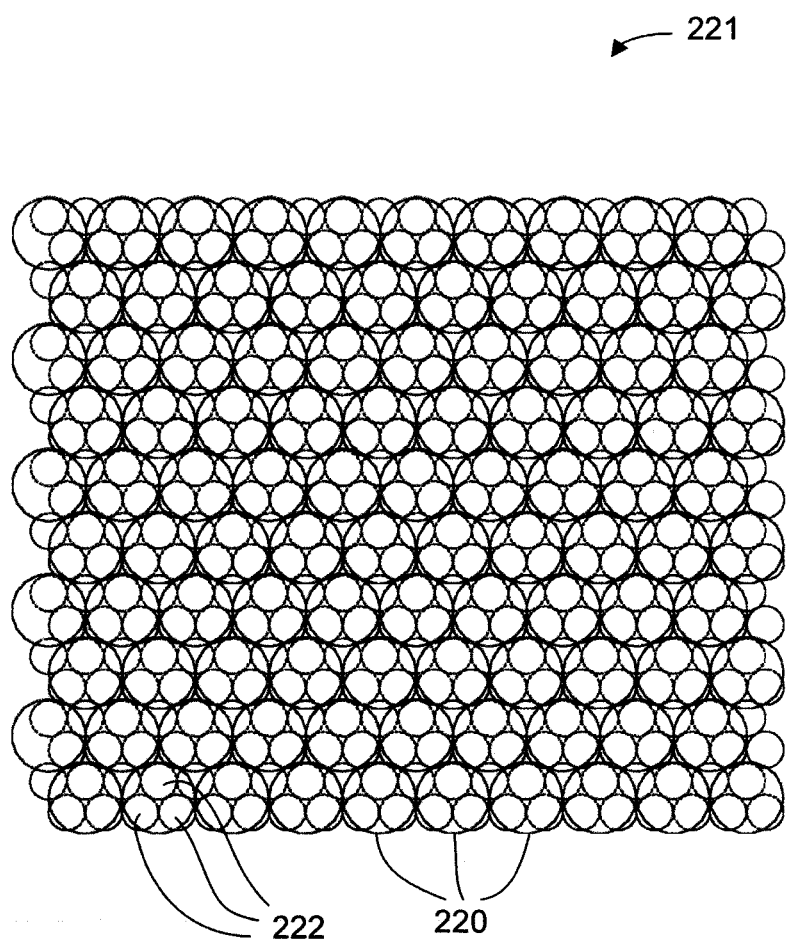
FIG. 18 is a diagrammatic illustration of another embodiment of ends of two imaging fibers.

Referring now to FIG. 18, in conjunction with FIG. 13 the former is a graphical representation of an embodiment of the imaging fiber-to-fiber connection of connector 166 (FIG. 13) in which fiber cores 220 of proximal end 184 of working assembly fiber bundle 174 and fiber cores 222 of distal end 188 of the imaging assembly imaging fiber bundle 170 are aligned in a suitable butt-coupled configuration. In this embodiment, the image can be transferred using the butt-coupled interface shown with less blur and light loss than occurs when using the simple butt-coupled interface illustrated in FIGS. 15-17. Fiber cores 220 are relative larger than fiber cores 222 and as a result in the butt-coupled configuration shown in FIGS. 13 and 18 image light from each of the relative larger fiber cores 220 will be transferred to multiple ones of the relatively smaller fiber cores 222, even in a situation in which the overall image circle of the working assembly fiber bundle is the same as the overall image circle diameter of the imaging assembly fiber bundle. The transfer of image light from the cores of the working assembly fiber bundle to the cores of the imaging assembly fiber bundle in the present embodiment does not depend on a rotational position of the fiber bundles relative to one another about a common longitudinal axis. No matter the relative rotational position of the fiber bundles, images from each core 220 will be transferred to multiple cores 222. As previously described, element densities are already maximized for white light, and individual fiber sizes may not be decreased due to chromatic effects. However, the imaging fiber bundle utilized with the single use working assembly can have a fiber density that is lower than the maximum.

In view of the foregoing Applicants recognize that it can be cost effective to use a relatively higher density image fiber bundle in the imaging assembly since the higher density image fiber bundle can be re-used multiple times. On the other hand, a relatively lower density image fiber bundle can be used for the working assembly imaging fiber to reduce the cost of the working assembly so that the working assembly can be a single use item. The lower fiber density bundle can also be more flexible than the higher fiber density bundle, which can make the lower fiber density bundle more suitable for use in the working assembly. The connector disclosed herein can provide an essentially distortion free transfer of the image from the disposable endoscope working assembly to the imaging assembly. The combination of decreased size and the mass production of at least one critical component can enable an economical realization of a disposable endoscope working assembly.

Figure 19:
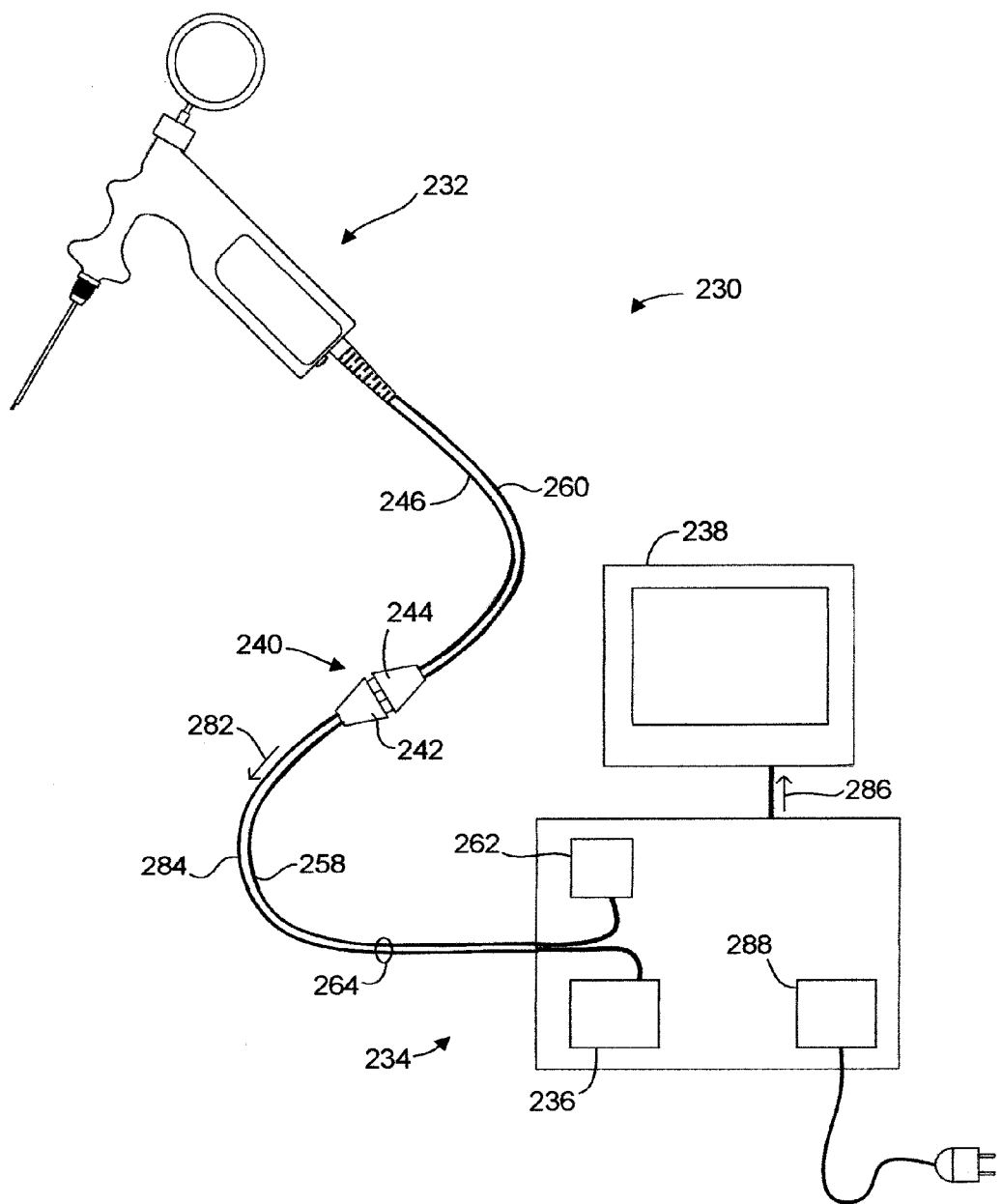
FIG. 19 is a diagrammatic illustration of another embodiment of an endoscope.
Figure 20:
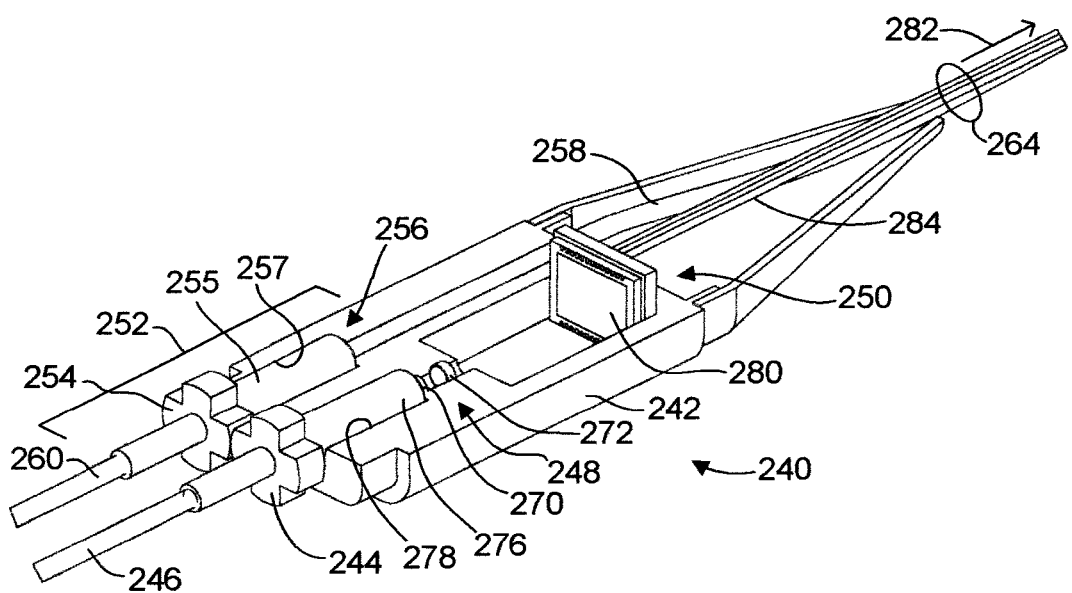
FIG. 20 is a diagrammatic cut away perspective illustration of another embodiment of a connector for connecting a working assembly and an imaging assembly of the endoscope shown in FIG. 19.

Referring now to FIG. 19, in conjunction with FIG. 20, another embodiment of an endoscope is shown diagrammatically and is generally indicated by the reference number 230. Endoscope 230 includes a working assembly 232 and an imaging assembly 234 having an imaging processor 236 and a viewing device 238. Endoscope 230 also includes a connector 240 having an imaging assembly connector fitting 242 and a working assembly connector fitting 244 (FIG. 20) which are configured to physically engage one another to optical couple an image from a working assembly imaging fiber bundle 246 through an optical assembly 248 (FIG. 20) to an electronic imaging sensor 250.

Connector 240 also includes an illumination fiber connector portion 252 which has a working assembly illumination fitting 254 and an imaging assembly illumination fitting 256 for optically coupling an imaging assembly illumination fiber 258 to a working assembly illumination fiber 260 to provide illumination from an illumination source 262 (FIG. 19) to the working assembly. Working assembly illumination fitting 254 supports working assembly illumination fiber 260 and imaging assembly illumination fitting 256 supports imaging assembly illumination fiber 258. Illumination source 262 (FIG. 19) provides light through the illumination fibers to illuminate a field of view of the working assembly at a distal end. In one embodiment, working assembly illumination fitting 254 includes a ferrule 255 and imaging assembly illumination fitting defines a bore 257 which are configured such that the ferrule engages the bore to align the working assembly illumination fitting and imaging assembly illumination fitting to optically couple the illumination fibers.

Optical assembly 248 includes an active optical element 270 and secondary optics 272. In an embodiment that is intended to minimize or reduce the size of the connector, the optical assembly can be configured as small as possible, therefore the active optical element and the secondary optics can be positioned as close to one another as possible in a manner that is consistent with the description above, for example, with respect to FIGS. 6 and 7. In order to minimize the distance between the active optical element and the secondary optics, a distal focal plane of the optical assembly can be essentially at a distal surface of the active optical element.

In the illustrated embodiment, the working assembly connector fitting includes a ferrule 276 and the imaging assembly connector fitting includes a bore 278. When the working assembly connector fitting engages the imaging assembly connector fitting, a proximal end of the fiber cores of the working assembly imaging fiber is positioned in three dimensions in the focal plane of optical assembly 248 to within a sub-micron tolerance, as described, for example with respect to FIGS. 6 and 7. A proximal focal plane of the optical assembly 248 is essentially co-planar with a sensor array surface 280 of electronic imaging sensor 250. A magnification ratio of the optical assembly can be one-to-one or larger such that the optical assembly can optically couple an image pixel from a single fiber core of the working assembly imaging fiber to one or more light sensor pixels of the electronic imaging sensor. The secondary optics can be configured to correct for spatial and/or chromatic aberration.

The electronic imaging sensor can be a CCD array or other suitable electronic device that receives images and produces a video signal 282 (FIG. 19) in response. The electronic imaging sensor can be electrically connected to imaging processor 236 by an electrical cable 284 and the imaging processor can convert video signal 282 into a video signal 286 having a format for producing an image viewable by a person on viewing device 238. Imaging assembly 234 can include a power supply 288 to provide power to the electronic imaging sensor (and other devices), through electrical cable 284, which can be a multi-conductor cable. One of the benefits of having the electronic image sensor in the connector resides in allowing a cable 264 connecting the connector to the body of the instrument to be extremely small and flexible. Miniature CCD arrays are manufactured in large quantities for applications such as cell phone cameras and are therefore relatively inexpensive. The connector can be configured such that the imaging fiber of the working assembly of the endoscope imposes the most significant limitation to resolution. For example, if a six thousand element imaging fiber is employed to transfer the image from the distal optics to a one million pixel ccd array, the resolution will be constrained primarily by the six thousand elements of the imaging fiber.

Figure 21:
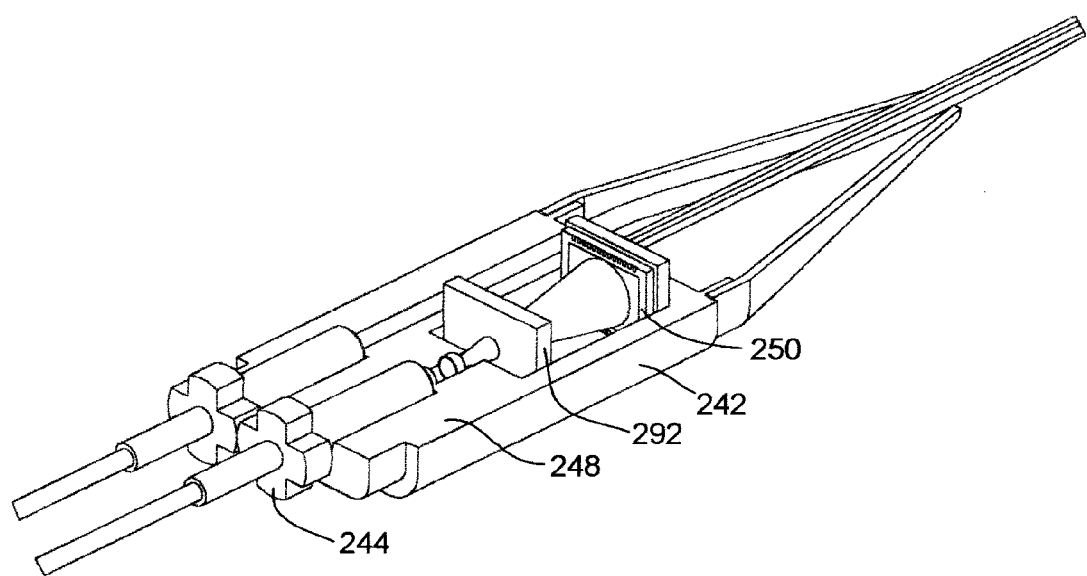
FIG. 21 is a diagrammatic cut away perspective illustration of another embodiment of a connector.

Referring now to FIG. 19 in conjunction with FIG. 21, in an embodiment, the imaging assembly connector fitting can include an optical filter 292. The filter can be permanently attached to the imaging assembly connector fitting or can be removable. The filter can be positioned in front of electronic imaging sensor 250 for use in spectroscopic discrimination, such as for fluorescence measurement. In a fluorescence measurement, ultra-violet (UV) or near UV light can be supplied by the light source through the illumination fiber to tissue in the field of view of the objective lens. The UV light can be used to excite visible wavelength fluorescence in the tissue. Optical filter 292 can block a UV pump beam light from the illumination source but can allow the visible fluorescent radiation through to the electronic imaging sensor to image the fluorescence. One or more other wavelength or spatially discriminatory elements, such as for example, a grating and/or pinhole pattern arrangement may be included. The fluorescent image is then converted to a video signal and transmitted to the imaging assembly where the fluorescent-based image can be viewed by a person. Further, the electronic imaging sensor itself can be particularly suited for viewing infrared or ultraviolet images instead of the visible spectrum. Matching optics and an infrared or ultraviolet transmitting fiber, such as a photonic crystal imaging fiber, can be employed in the disposable working assembly. As illustrated by the foregoing embodiment, a connector containing an electronic imaging sensor can perform more than simple imaging.

Figure 22:
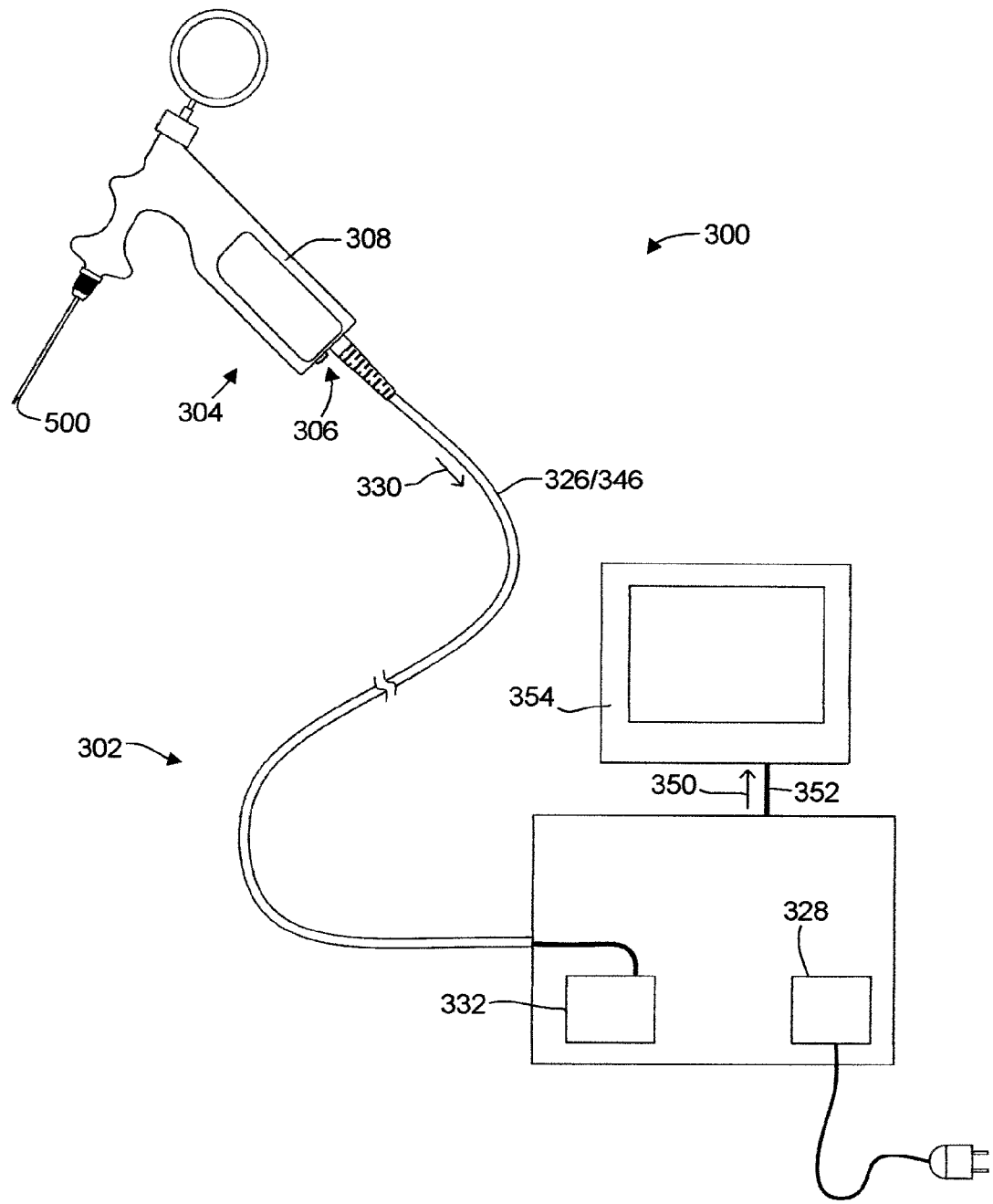
FIG. 22 is a diagrammatic illustration of another embodiment of an endoscope.
Figure 23:
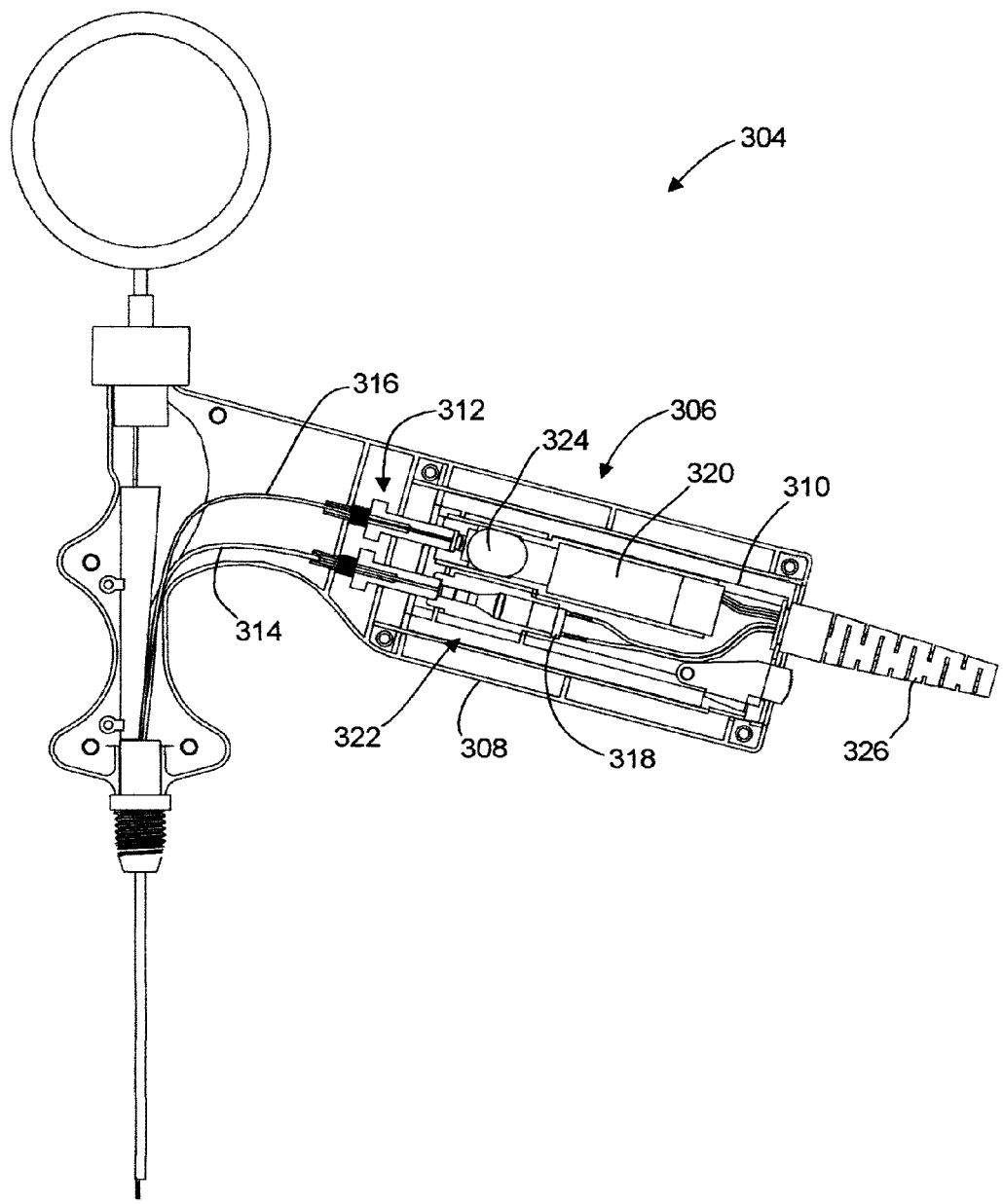
FIG. 23 is a diagrammatic cut away illustration of another embodiment of a connector.

Referring now to FIGS. 22 and 23, an endoscope 300 is illustrated including an imaging assembly 302 and a working assembly 304. Endoscope 300 can include a connector 306 (FIG. 23) that is integrated in a handle 308 of the working assembly. Connector 306 can have an imaging assembly connector fitting 310 and a working assembly connector fitting 312.

The working assembly includes an imaging fiber 314 and an illumination fiber 316 that are optically coupled to the imaging assembly connector fitting 310. In an embodiment, the imaging assembly connector fitting includes an electronic image sensor 318 and a light source 320. Imaging fiber 314 is optically coupled to the electronic image sensor 318 of types such as, for example, those described above, using an optical assembly 322 which can include an active optical element and secondary optics for magnification and a proximal end of the imaging fiber can contact the active optical element when the connector fittings are engaged. Light source 320 can utilize a standard focusing lens 324 to optically couple light generated by the light source to the illumination fiber. A multiple conductor electrical cable 326 can provide power from a power source 328 to the illumination source and electronic image sensor and can carry a video signal represented by arrow 330, generated by the electronic image sensor in response to receiving images from the imaging fiber bundle, to an imaging processor 332. It should be appreciated that in this embodiment cable 326 extends between the working assembly and an imaging assembly and does not utilize an optical fiber. Therefore, cable 326 can be relative small in diameter, flexible and inexpensive.

Figure 24:
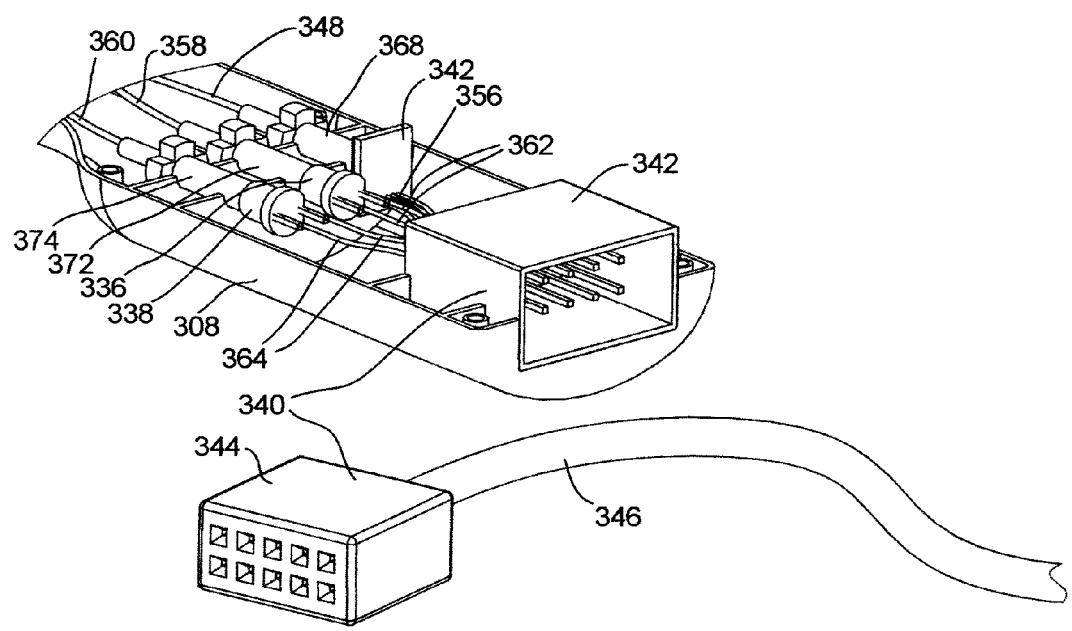
FIG. 24 is a diagrammatic cut away illustration of another embodiment of a connector.

In another embodiment illustrated in FIG. 24, in conjunction with FIG. 22, an electronic imaging sensor 334 and illumination sources 336 and 338 are included as part of the working assembly and are located in handle 308 of working assembly 304. In this embodiment, a connector 340 is an electrical connector that is arranged to electrically connect the working assembly to the imaging assembly. The electrical connector includes a working assembly connector fitting 342 and an imaging assembly connector fitting 344 that engage one another to transfer electrical signals and power. The imaging assembly includes a cable 346 attached to the imaging assembly connector fitting that carries power to the electronic imaging sensor and the illumination source from power source 328 and carries video signals 330 back to the imaging assembly from the electronic imaging sensor to processor 332 in the imaging assembly. The working assembly includes a cable 356 that carries video signals and power between working assembly connector fitting 342 and electronic imaging sensor 334. Video signals 330 can be generated by the electronic imaging sensor in response to receiving images from a distal end of an imaging fiber bundle 348 of the working assembly. The processor can receive video signals 330 and can produce video display signals 350 in response, which can be transferred through a display cable 352 to a display 354 for viewing.

Illumination sources 336 and 338 can generate light and can focus the generated light into illumination fibers 358 and 360, respectively, which can guide the light to the distal end of the probe of the working assembly. The illumination source can receive power through electrical conductors 362 and 364 from working assembly connector fitting 342. The processor can control the illumination source using power from power source 328 through cable 346 and conductors 362 and 364 to turn the illumination sources on and off individually or together. Ferrules 372 and 374 can be attached to illumination fibers 358 and 360, respectively, and can be used for aligning the illumination fibers with illumination sources 336 and 338, respectively, to promote light transfer from the illumination sources to the illumination fibers. Although only two illumination sources and two illumination fibers are shown, the working assembly can include more than two of each.

In an embodiment of the working assembly shown, imaging fiber 348 can be optically coupled to electronic imaging sensor 336 using butt-coupling. When the electronic imaging sensor, such as a CCD array, has an element size (i.e., pixel diameter or width) that is equal, or preferably, smaller than the size of the fiber core ends of the imaging fiber (i.e. sub 4 microns) the imaging sensor can simply be butt-coupled and glued to the imaging fiber. The spacing between the imaging fiber and the imaging sensor can be minimal or zero. A ferrule 368 can be attached to imaging fiber 348 and the ferrule can be used to align the end of the imaging fiber with the electronic imaging sensor such that image from each fiber core of the imaging fiber are received by at least one sensor pixel of the electronic imaging sensor. For reasons stated previously, the cost of electronic image sensors, such as CCD arrays and LEDs, have dropped to the point where their integration into a disposable working assembly of an endoscope is economically feasible. In such a case, the connector can be electrical and there then is no need for an optical transfer of the image.

Figure 25:
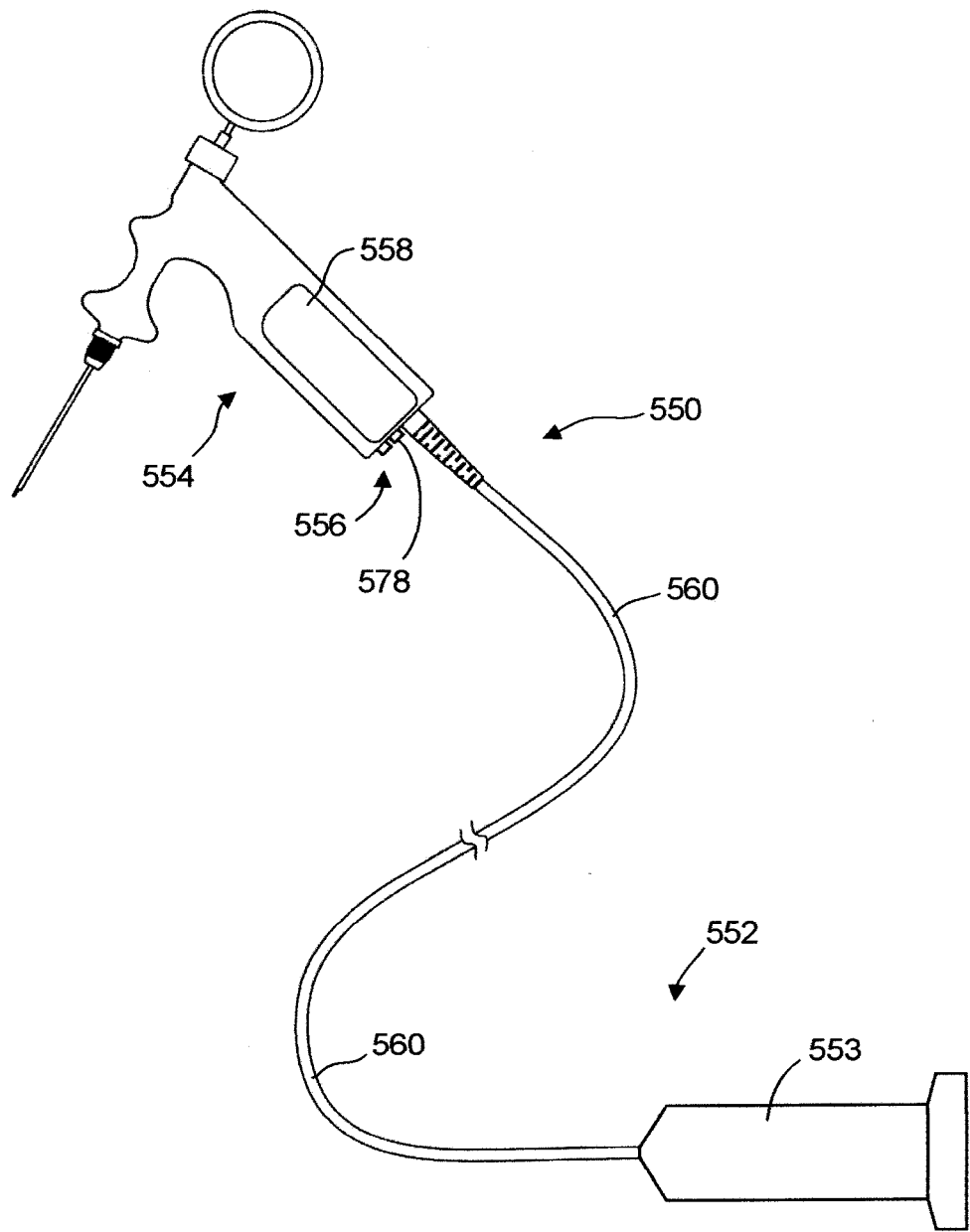
FIG. 25 is a diagrammatic illustration of another embodiment of an endoscope.
Figure 26:
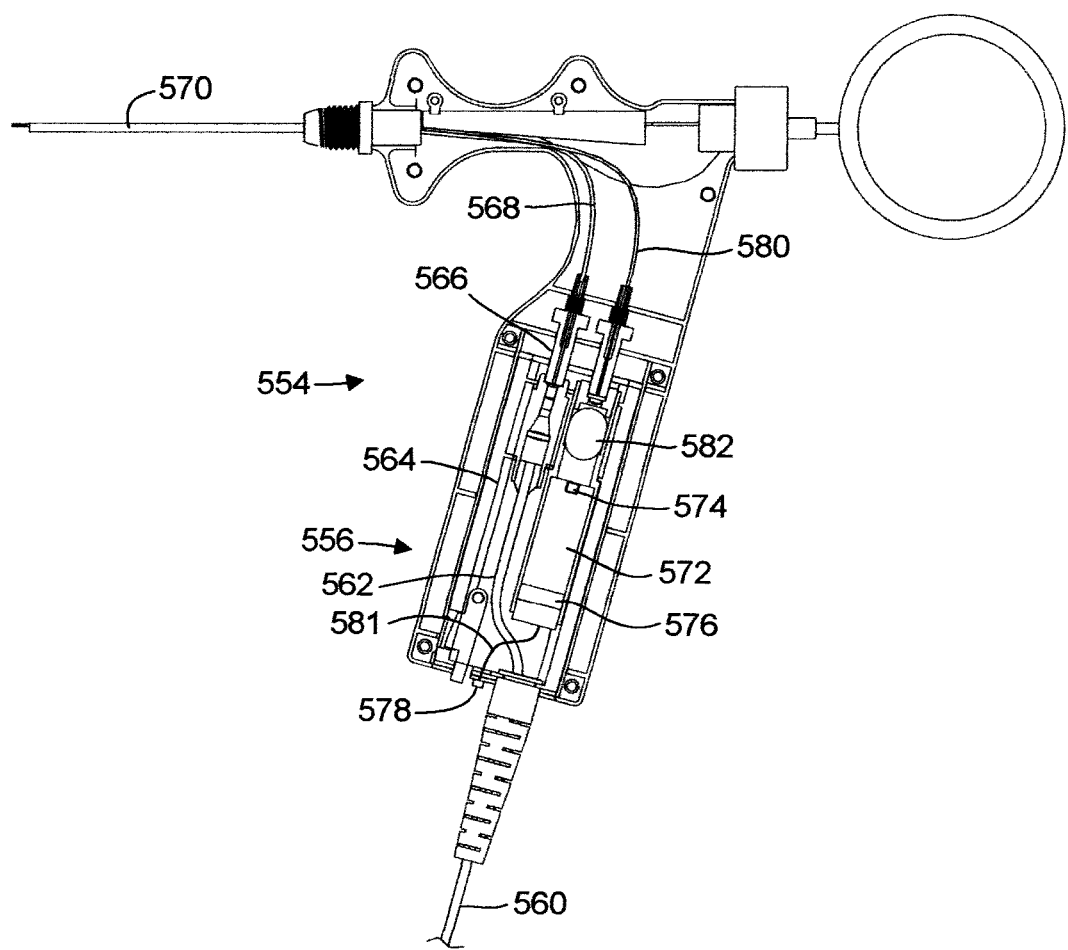
FIG. 26 is a diagrammatic cut away illustration of another embodiment of a connector.

In an embodiment, shown in FIGS. 25 and 26, an endoscope is shown diagrammatically and is generally indicated by the reference number 550. Endoscope 550 includes an imaging assembly 552 and a working assembly 554 that is optically coupled to the imaging assembly using a connector 556 that is integrated into a handle 558 of the working assembly. Imaging assembly 552 includes a cable 560 that has an imaging fiber bundle 562 (FIG. 26) that extends from an imaging assembly connector fitting 564 of connector 556 to an eyepiece 553 of imaging assembly 552. Connector 556 includes a working assembly connector fitting 566 that cooperates with imaging assembly connector fitting 564 to optically couple imaging assembly imaging fiber 562 to a working assembly imaging fiber 568. Eyepiece 553 can focus on the proximal end of imaging fiber bundle 562 using one or more optical elements to image the proximal end of the imaging fiber bundle and to magnify the image. The working assembly can image a field of view of the working assembly at a distal end of a probe 570 and the image can be transferred through imaging fiber 568 of the working assembly to connector 556 which optically couples the image to imaging fiber 562. The image can then be transferred through imaging fiber 562 to the eyepiece where the image can be viewed.

Imaging assembly connector fitting 564 can include an illumination source 572 which can have a light 574 such as an LED, a power source such as battery 576 and a control 578 such as a switch electrically connected to the battery using an electrical conductor 581 for selectively turning the illumination source on or off. Illumination source 572 can utilize a standard focusing lens 582 to optically couple light generated by the illumination source to an illumination fiber 580. Illumination fiber 580 can transfer the illumination to the distal end of probe 570 to illuminate the field of view of the working assembly. Although illumination source 572 is shown as part of the imaging assembly connector fitting, which can be reused with multiple working assemblies, the illumination source can be included in the working assembly. In an embodiment in which the illumination source is integrated in the working assembly, the illumination source can be optically coupled to the illumination fiber of the working assembly without using the connector and the control can be integrated into working assembly.

Figure 27:
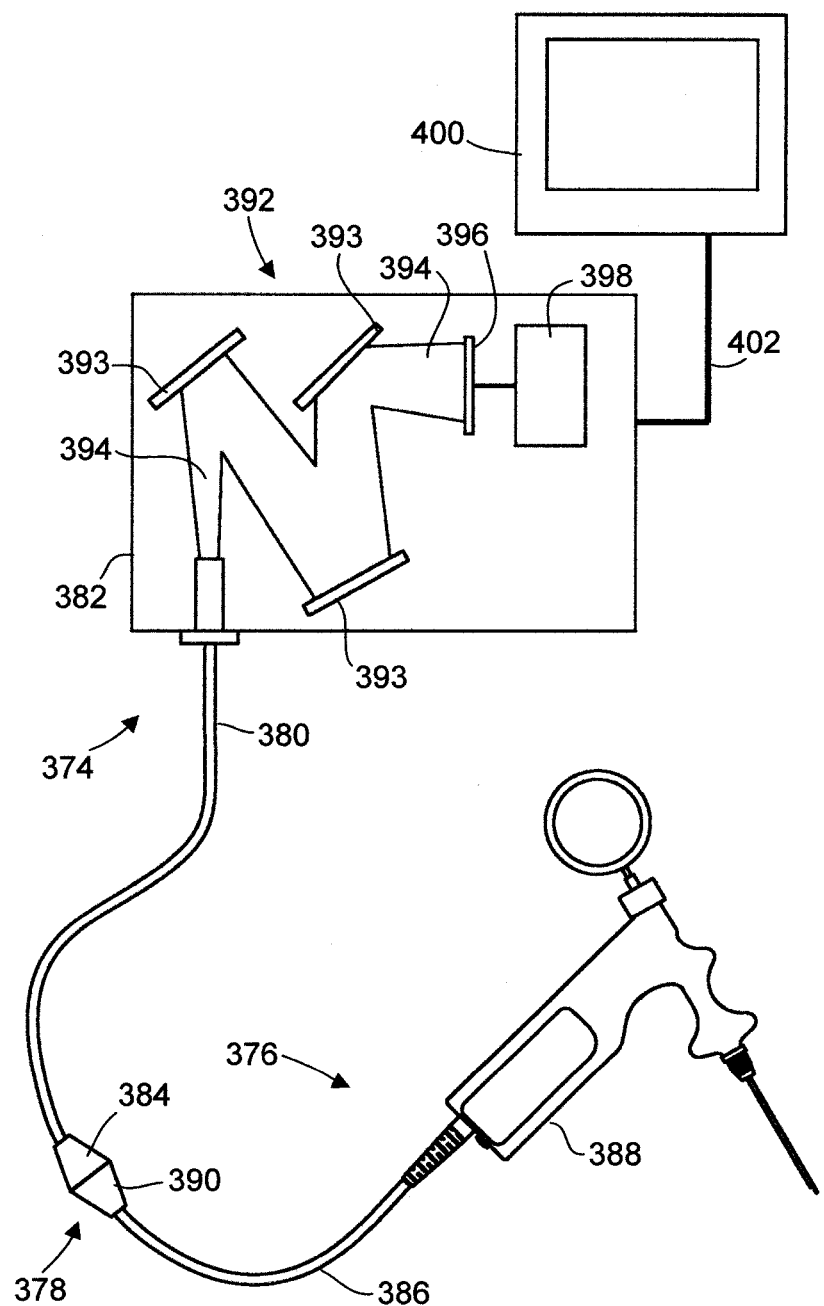
FIG. 27 is a diagrammatic illustration of another embodiment of an endoscope.

Attention is now directed to FIG. 27 in which an endoscope is shown diagrammatically and is generally indicated by the reference number 372. Endoscope 372 includes an imaging assembly 374 and a working assembly 376 that is optically coupled to the imaging assembly using a fiber-to-fiber connector 378. A cable 380 includes an imaging fiber bundle and extends between an imaging assembly housing 382 and an imaging assembly connector fitting 384. A cable 386 includes an imaging fiber bundle that extends from a handle 388 of the working assembly to a working assembly connector fitting 390. The imaging fiber-to-imaging fiber connector can also be integrated into the working assembly handle and can include one or more illumination sources, or the illumination source can be in the imaging assembly.

Applicants recognize that one of the benefits to employing a fiber-to-fiber connector, such as a fiber-to-fiber magnification connector, occurs when the image light from the distal object contains more information than simply an image. By utilizing a fiber-to-fiber connector, image light 394 can be delivered from the working assembly to the imaging assembly and then to the body of the instrument where more sophisticated signal/image processing employing devices can be mounted that may otherwise be too large to fit into the connector assembly. The individual imaging fibers can propagate the amplitude of the light of the image, but coherence of the light from one fiber to the next is lost during the propagation. Each fiber core of the imaging fiber bundle can act as an individual source with image light phase information that is randomized relative to image light from other fiber cores. While some signal/image processing techniques require spatial coherence of the image, and therefore direct optics without separating the image into pixels using the fiber cores, other, fairly complex, signal/image processing does not require spatial coherence of the image. Some examples of techniques for determining light characteristics that do not require spatial coherence are: barrel distortion correction, lateral chromatic aberration correction, stereoscopic imaging, synthetic depth perception given different illumination angles, and spectroscopy of the sampled radiation, to name a few. Using the spectral characteristics of the gathered light by way of non-limiting example, it can be beneficial to transfer that light to diagnostic tools in the body of the instrument where a mono-chrometer, spectrometer or similar discrimination device (all of which require space) can be employed to characterize the imaged radiation.

The imaging assembly, in the present embodiment, includes a grating arrangement 392. The grating arrangement can include grates 393 be employed to separate different wavelengths of image light 394 from one another to determine if specific wavelengths of light have been absorbed, or in the case of fluorescence, to determine if a specific wavelength of the light has been emitted. The grating arrangement can include an electronic image sensor 396 for sensing the light and producing an electrical signal and an imaging processor 398 for electronically processing the electrical signal to extract information related to the image light. The imaging assembly can display images and/or results of the processing on a display 400 delivered by a cable 402.

Figure 28:
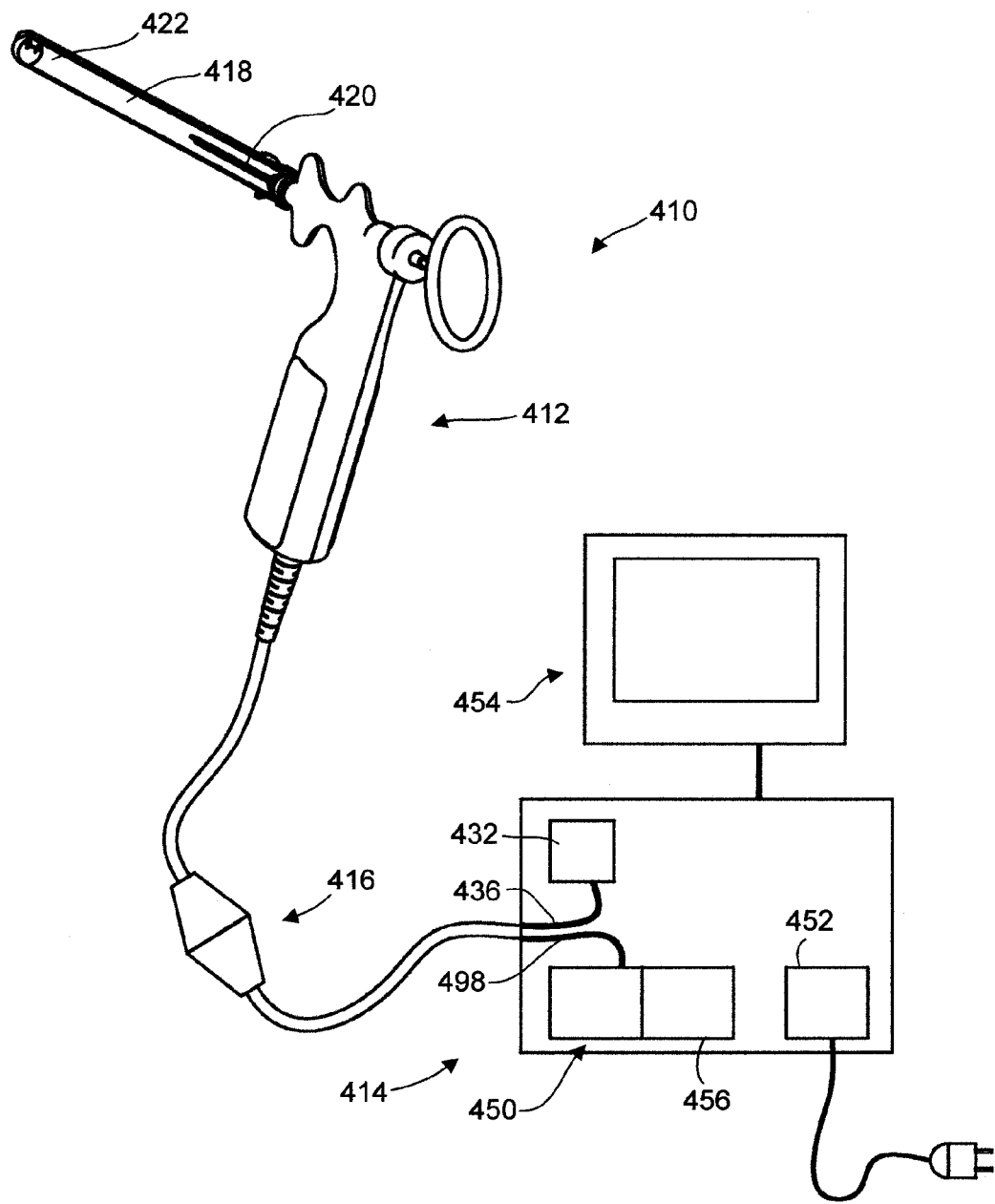
FIG. 28 is a diagrammatic illustration of another embodiment of an endoscope.
Figure 29:
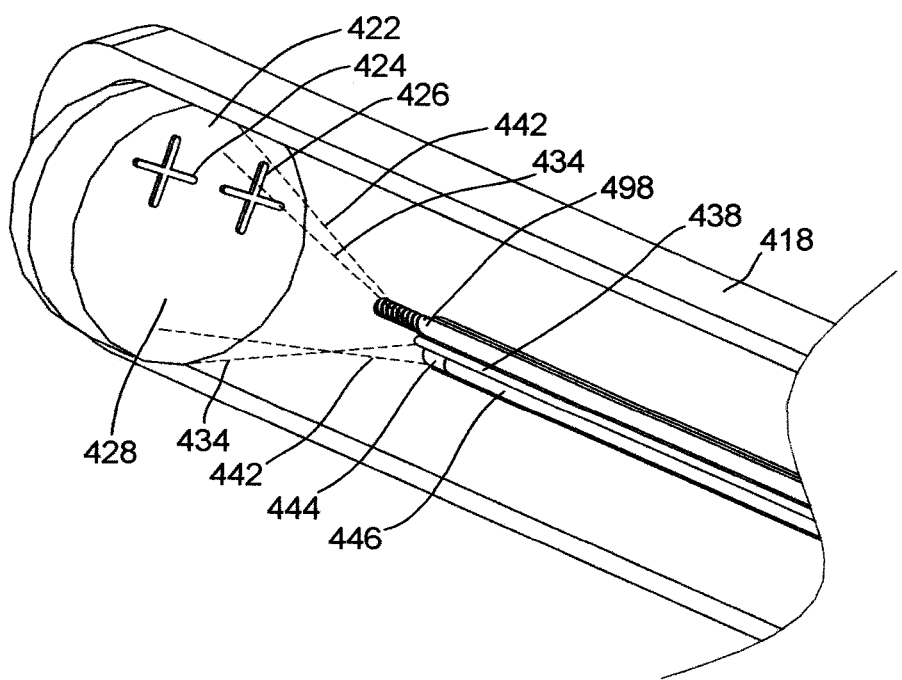
FIG. 29 is a diagrammatic cut away illustration of a distal end of a probe of the endoscope and a predetermined image of a package assembly.

Referring now to FIG. 28 and FIG. 29, an endoscope 410 includes a working assembly 412 connected to an imaging assembly 414 by a connector 416. The working assembly can be received in a packaging arrangement 418, which can also be referred to as a cap and which can serve as a protective cover for a probe 420 of the working assembly. The probe can be a flexible or rigid structure and can include an imaging fiber bundle, a distal objective lens, an illumination fiber and a working channel, not shown in FIG. 28. The packaging arrangement can be removably attached to the working assembly and can protect and maintain the sterility of the probe prior to the use of the working assembly in a surgical procedure.

The packaging arrangement can be used to perform a calibration of the endoscope. The packaging arrangement can be configured to include a predetermined picture, for example predetermined picture 422 shown in FIG. 28 and in further enlarged view of FIG. 29. Picture 422 can be located in a field of view of the working assembly objective lens when the packaging arrangement is positioned on the working assembly probe. The predetermined picture can include one or more patterns, shapes, colors and/or seamless backgrounds. Picture 422, by way of non-limiting example, includes a blue shape 424, a red shape 426 and a white seamless background area 428. The predetermined picture can also include texture, for example in predetermined picture 422, the blue and red shapes 424 and 426 can be engraved into the surface of the material of the packaging arrangement. The texture can be a variation in a surface such as, for example, by including different depths or elevation changes.

The imaging assembly can include an illumination source 432 (FIG. 28) that provides light 434 as indicated by dashed lines (FIG. 29) through an imaging assembly illumination fiber 436 coupled to a working assembly illumination fiber 438 by connector 416. The light from the illumination fiber shines on a field of view 442, represented by dashed lines, of objective lens 444. A working assembly imaging fiber bundle 446 guides the image light from the objective lens to the connector which optically connects imaging fiber bundle 446 to an imaging fiber bundle 448 which carries the image to an imaging processor 450. A power supply 452 powers the endoscope and images generated by the endoscope can be viewed on display 454.

The objective lens images the image field, which in this case includes the predetermined picture, and the imaging fiber bundles convey a predetermined picture image of the predetermined picture to the imaging processor. In an embodiment, the imaging processor includes a calibration configuration 456. The calibration configuration can utilize an electronic image sensor, for converting the received image into electrical video signals, a processor and memory, which can be included in the imaging processor and/or calibration configuration.

An image can be received by the imaging processor can include distortion characteristics introduced by one or more of the optical elements between the image field and the calibration configuration. The calibration configuration includes a calibration image standard in memory which contains information based on the actual appearance of predetermined picture 422 in the absence of distortion. The calibration configuration compares the predetermined picture image that contains the distortion characteristic to the calibration image standard and produces a calibration mask which can thereafter be applied to any other image that is received by the imaging assembly to correct the distortion characteristics to produce an accurate representation of the image field, which can then be sent to display 454 for viewing by a person. In an embodiment, multiple calibration masks can be produced and combined or used separately to compensate for multiple different distortion characteristics.

In one embodiment, white seamless background 428 can be positioned on one half of the predetermined picture and can be used to perform a "white balance" to ensure that the colors perceived are accurate. Blue shape 424 and red shape 426 can be positioned on the other half of the predetermined picture and can be used for measuring chromatic aberration and image distortion. In an embodiment, different portions of the predetermined picture can be positioned in the field of view by rotational movement of the packaging arrangement. For example, the white seamless background can be positioned in the field of view and the "white balance" calibration can be performed. The packaging arrangement can be rotated 180 degrees to move the blue and red shapes into the field of view and the chromatic aberration and spatial aberration calibration can then be performed. Image distortion characteristics can be caused, for example, by the objective lens, the connector, the imaging fiber bundle, the imaging fiber cores and the spaces between the imaging fiber cores. In some instances, a distinctive pattern can be included on the predetermined picture, which can also be referred to as a calibration background. The distinctive pattern can be used for even more elegant and/or complex calibrations.

Figure 30:
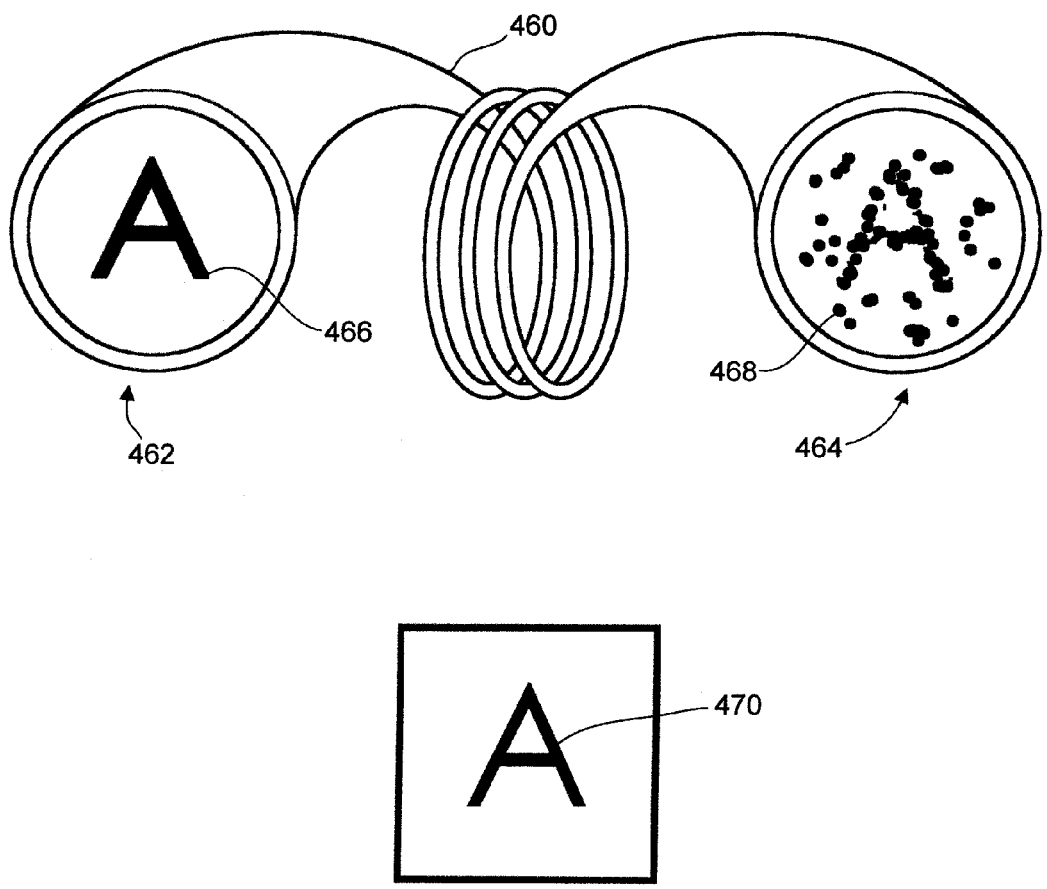
FIG. 30 is a diagrammatic illustration of a non-spatially consistent imaging fiber and a corrected image.

Referring now to FIG. 30 in conjunction with FIG. 5, in some instances an imaging fiber bundle can be spatially consistent with itself which results in an image at one end appearing essentially the same as at the other end, as is shown in FIG. 5. In contrast, an imaging fiber bundle 460, FIG. 30, can have imaging fiber cores that are not spatially consistent from a first end 462 to a second end 464. In this situation, an image 466 at the first end is not accurately represented spatially through the imaging fiber bundle and an image 468 at the second end exhibits a spatial distortion characteristic in comparison to the image at the first end. Given the calibration mask, imaging assembly 414, (FIG. 28), can convert the spatially distorted image into a corrected image 470 that essentially accurately represents image 466 at the first end of the imaging fiber bundle.

Figure 31:
FIG. 31 is a picture representing an image seen through an imaging fiber with a butt-couple connection that has been corrected.

Referring again to FIGS. 14 and 16, the image through the imaging fiber bundle can exhibit a "chicken wire" effect caused by a relatively dark pattern that looks similar to chicken wire, resulting at least partially from the common cladding in between the individual imaging fibers. While the cladding is required in order to allow low loss wave-guiding of the light in the fiber core, the cladding itself does not propagate the light and is therefore dark. The "chicken wire" pattern is another example of a distortion characteristic which can be at least partially corrected using interpolation and/or other image processing techniques performed by the calibration configuration given the calibration mask as discussed. Referring now to FIG. 31, a corrected image 478 can result from image 210 (FIG. 16) when the "chicken wire" of image 210 is removed or at least partially corrected using techniques described.

Referring again to FIG. 28, connector 416 can be a fiber-to-fiber connector from which the image is directly received by the calibration configuration in the imaging assembly; or can include an electronic image sensor, in which case the calibration arrangement receives a video signal from the electronic image sensor in the connector. A single imaging assembly that includes the calibration arrangement can be used with multiple different working assemblies, as described, and can generate unique calibration masks for each one such that distortion characteristics unique to each working assembly can be corrected.

Figure 32:
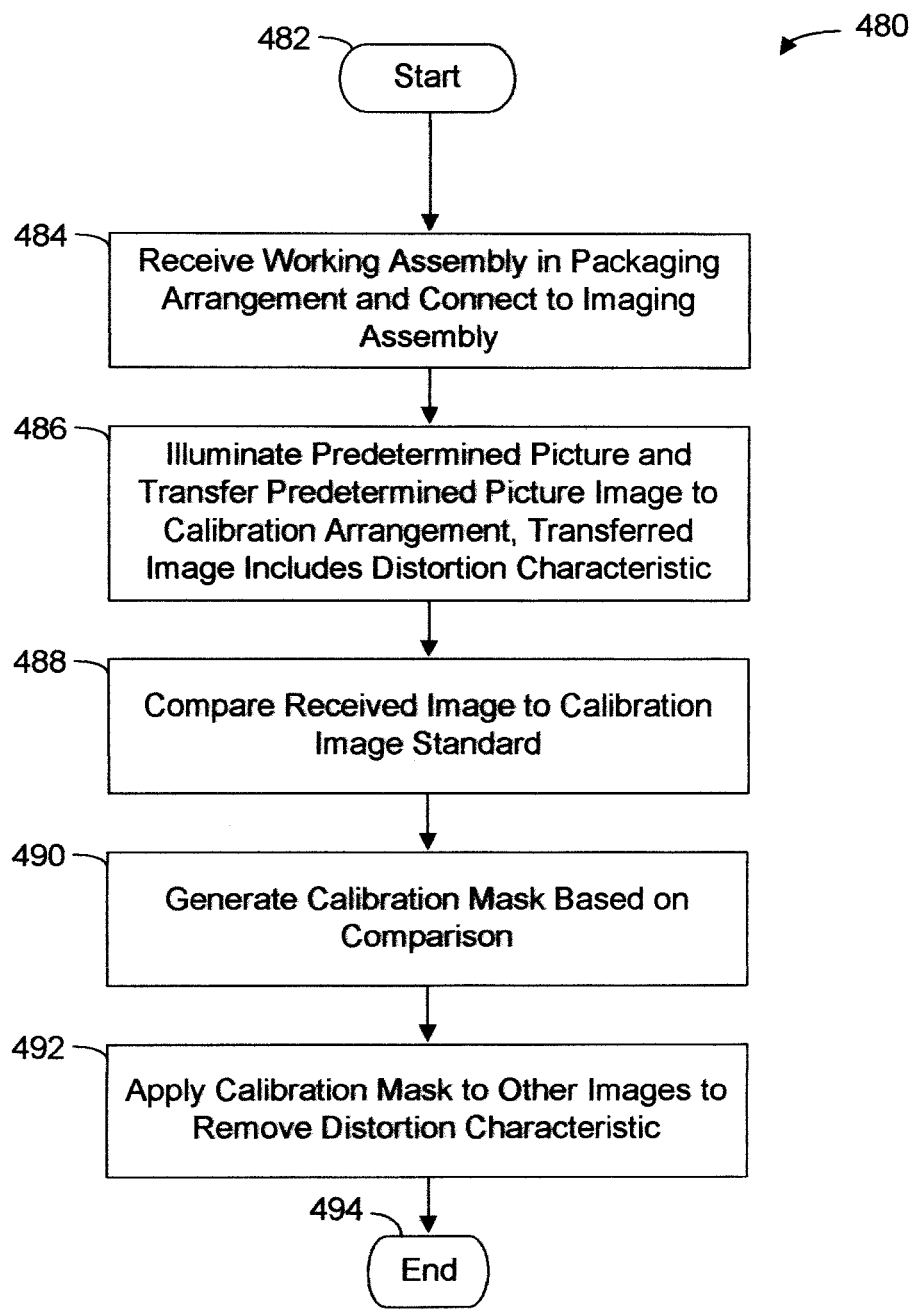
FIG. 32 is a flow diagram of a method for calibrating an imaging assembly and correcting an image.

Referring now to FIG. 32, a method for calibrating an imaging assembly to one of a plurality of working assemblies is shown and is generally referred to by reference number 480. Method 480 begins at start 482 and proceeds to 484 where a working assembly is received in a packaging arrangement having a predetermined picture in a field of view of the working assembly and is connected to an imaging assembly. Method 480 then proceeds to 486 where the predetermined picture is illuminated and a predetermined picture image is received through the working assembly by a calibration arrangement of the imaging assembly. The received image includes a distortion characteristic that causes the received image to be distorted relative to the predetermined picture. Method 480 then proceeds to 488 where the calibration arrangement compares the image received through the working assembly to a calibration image standard. Method 480 then proceeds to 490 where the calibration arrangement generates a calibration mask based on the comparison. Method 480 then proceeds to 492 where the calibration arrangement thereafter applies the calibration mask to other images received through the working assembly to remove the distortion characteristic. The other images can be images of tissue received by the imaging assembly during a surgical procedure, or other images of objects in the field of view of the working assembly during another endoscopic procedure. Method 480 then proceeds to 494 where the method ends.

The imaging assembly can include a hardware or software control to initiate the calibration process. The calibration process can be automatically or manually initiated. For instance the imaging assembly can include a button that is pressed by a person to initiate the calibration process once the working assembly is connected. As another example, the imaging assembly can automatically initiate the calibration process when a working assembly is connected.

Figure 33:
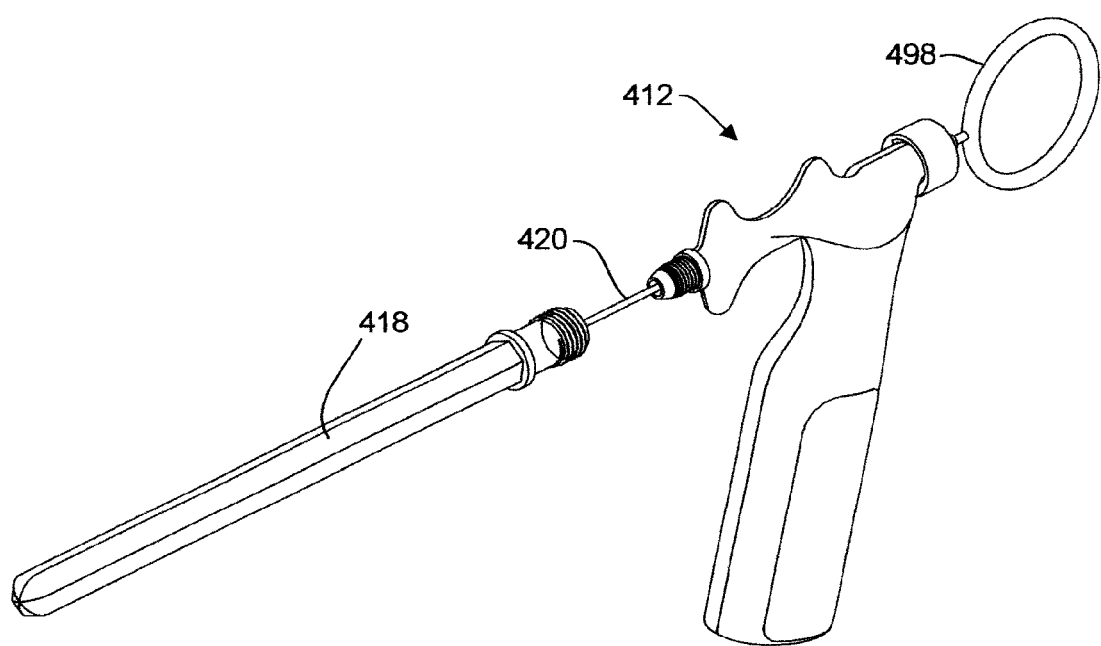
FIG. 33 is a diagrammatic perspective illustration of a working assembly and packaging assembly.
Figure 34:
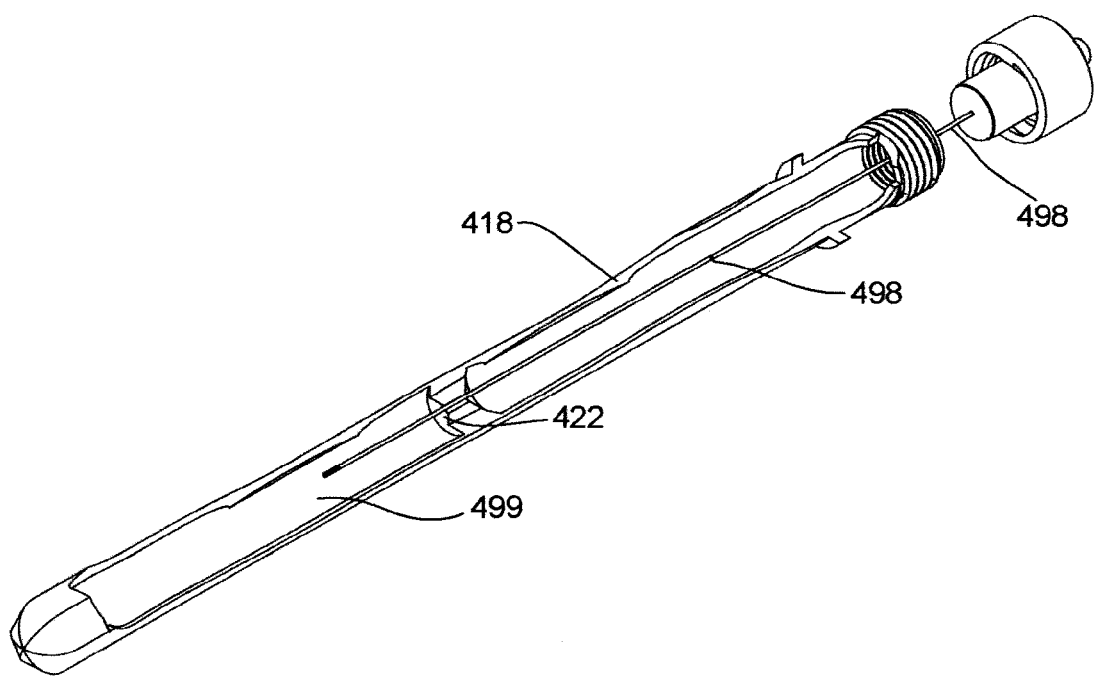
FIG. 34 is a diagrammatic perspective illustration of a packaging assembly and an endoscope tool.

Referring now to FIG. 33, in conjunction with FIG. 28, packaging arrangement 418 can be removed following the calibration. After an endoscopic procedure is performed, the packaging arrangement may be labeled and an endoscopy tool 498 may be removed from the working assembly with a tissue sample and placed back in the packaging arrangement for shipment to a lab, as illustrated in FIG. 34. In such a case, the endoscopy tool may need to pass through predetermined picture 422 and/or a membrane and into a gel 499 designed to preserve the sample. Such a gel could have other properties related to the sample collected.

Figure 35:
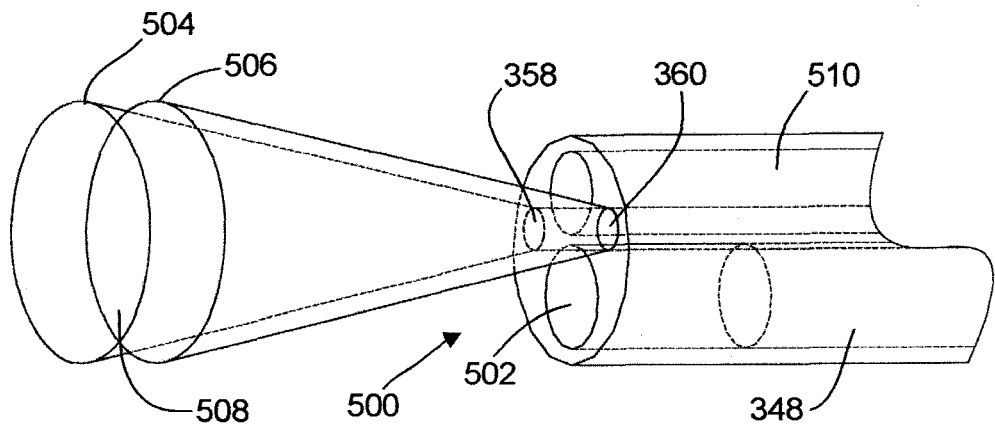
FIG. 35 is a diagrammatic partially transparent perspective illustration of a distal end of a working assembly with two illumination fibers.

Referring now to FIG. 35, in conjunction with FIGS. 22 and 24, in an embodiment, endoscope 300 (FIG. 22) includes an imaging assembly 302 and a working assembly 304 which can be connected together using a connector 340 (FIG. 24). The imaging assembly can include an imaging processor 332 for processing images from a field of view at a distal end 500 (FIG. 35) of the working assembly. Endoscope 300 includes two illumination sources 336 and 338 (FIG. 24) which are optically coupled to illumination fibers 358 and 360, respectively, shown in FIGS. 24 and 35. Although the two illumination sources are shown in the handle of the working assembly, there can be more than two illumination sources and the illumination sources can be housed in a connector located between the handle and the imaging assembly housing and/or located in the imaging assembly.

Figure 36:
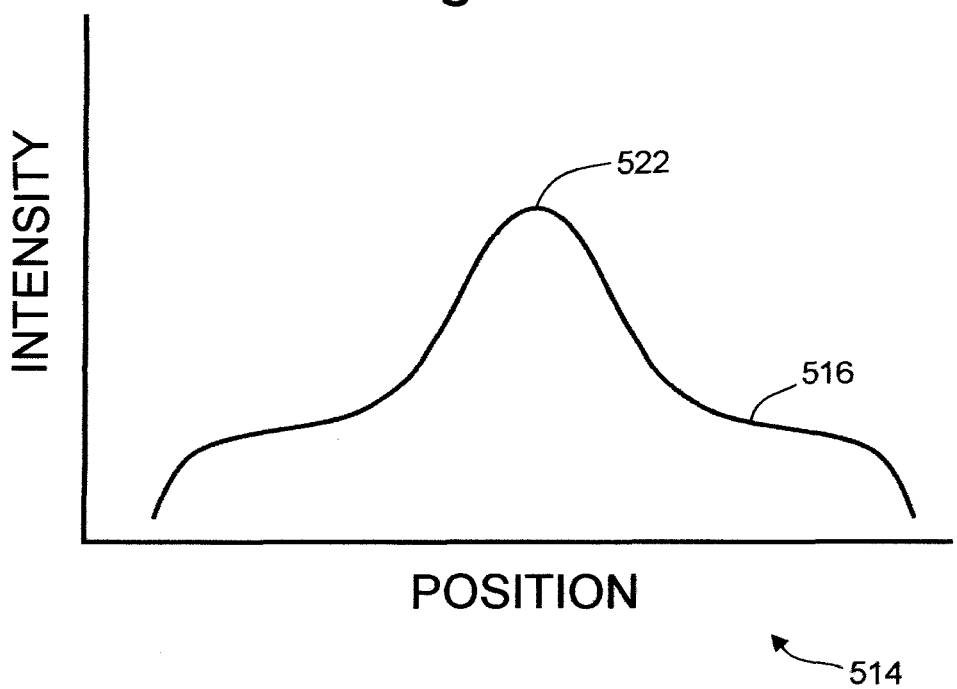
FIG. 36 is an intensity plot of light from a working assembly distal end with two illumination fibers.

Referring now to FIG. 35 an important aspect of endoscopy can be the ability to adequately illuminate the field of view of an objective lens 502 that is optically connected to imaging fiber bundle 348 at the distal end of the working assembly probe. Properly illuminating the field of view allows a person to see tissue in the body cavity and tools guided through a working channel 510 to the body cavity, used to manipulate the tissue. Adequate illumination is important regardless of whether white light is employed for image creation or if spectrally significant wavelengths are used for used for spectroscopy. Separate and dedicated large core (>30 um) fibers 358 and 360 can be used to deliver the illumination radiation. The fibers can be chosen to have a numerical aperture (NA) such that cones of light 504 and 506 from fibers 358 and 360, respectively, can overlap in an overlap area 508 within the viewing area of the imaging fiber bundle. Illumination fibers generally have an intensity distribution as shown by plot 514 of FIG. 36 which plots intensity 516 on a vertically against position. The two illumination sources can generate a relatively higher intensity peak 522 which can be referred to as a "hot spot." The "hot spot" can be generally intensified when spatially separated illumination fibers are used and where the beams overlap, such as at overlap area 508.

When spatially separated illumination fibers are used, the effect of a combined hotspot can be mitigated by synchronously alternating the illumination between fibers while capturing sequential images. The images can then be processed and the individual pixel gain adjusted before viewing the images. The illumination and individual pixel gain can be set by employing a calibration before use.

Endoscopes have historically utilized direct viewing during use, but recently there has been an increase in the use of camera systems for indirect, real time viewing. The matching development of high-speed semiconductor components dedicated to both signal and image processing has opened up a new paradigm of real-time signal, image and video processing. It is currently possible to purchase a consumer camera that can synthetically create a stereoscopic picture by capturing multiple frames of the same object from slightly different perspectives. This camera can take a sequence of twenty pictures while the camera is moved and can then automatically select the best two which will result in a true to life stereoscopic image. Such processing is referred to as photogrammetry and, more specifically for the generation of a stereoscopic image, stereophotogrammetry. Photogrammetry can be defined as determining the geometric properties of objects from photographic images.

Figure 37:
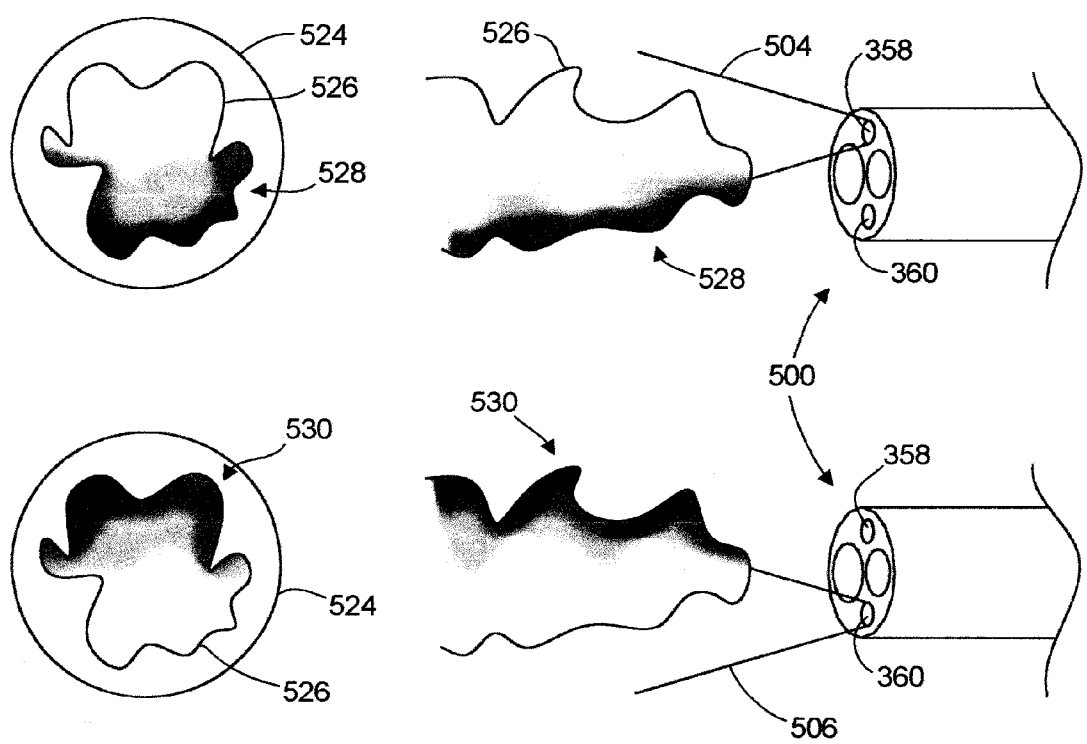
FIG. 37 is a diagrammatic perspective illustration of distal ends of a working assembly with light from illumination fibers.

Referring now to FIG. 37 in conjunction with FIG. 35, an object 526, such as tissue, is shown in a field of view 524 of objective lens 502 of the working assembly 304. Illumination fibers 358 and 360 can be synchronized to separately illuminate the field of view with cones of light 504 and 506, respectively. Because the illumination fibers are spatially separated, synchronously illuminating the object and recording images can result in images that exhibit different shadows when irregular shapes are being viewed. For instance, when illumination fiber 358 emits cone of light 504 a shadow 528 appears on one side of the object; and when illumination fiber 360 emits cone of light 506 a shadow 530 appears on another side of the object. These different shadows can be utilized by imaging processor 332 (FIG. 22) to generate a synthetic stereoscopic image which can then be displayed on viewing device 354. This is different than the previously described stereophotogrammetry in that the imaging, objective lens 502 does not move during the synchronous illumination and image recording; it remains in the same place. It is the position of the illumination that is different, not the position of the imaging lens. Unlike a conventional shape from shadow technique, the illumination is modulated between two different angles as pictures are recorded because of the two different positions of the illumination fibers at the distal end of the working assembly. The imaging assembly can be calibrated, as described above, to remove any distortion characteristics prior to using the synchronous illumination techniques described. A calibration object can be consistently used to improve the process from picture to picture. This alleviates the heavy computing that would typically be required to generate a three-dimensional image and then derive a stereo image.

Figure 38:
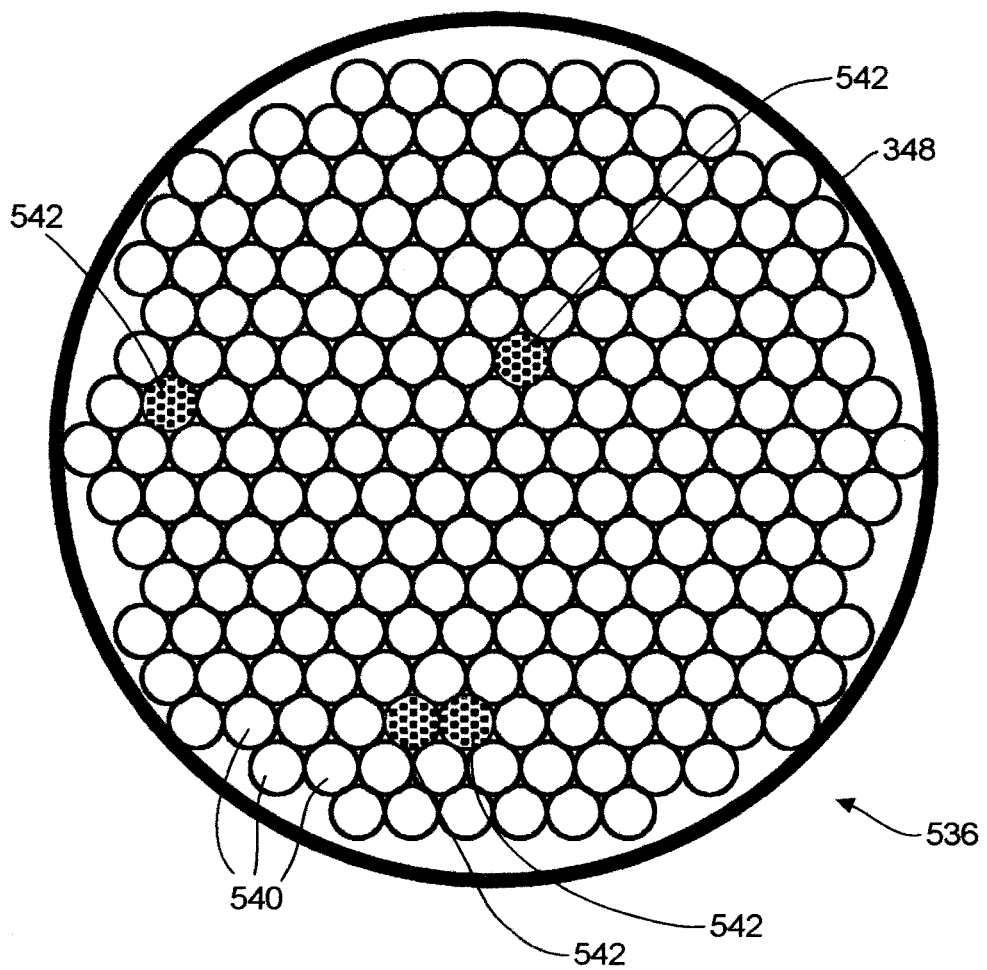
FIG. 38 is a diagrammatic illustration of an end of an imaging fiber bundle with defective fiber cores.
Figure 39:
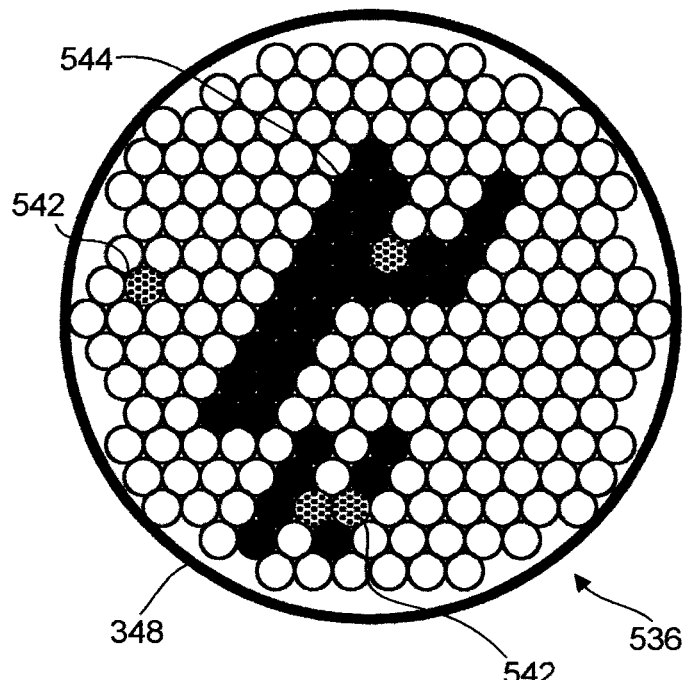
FIG. 39 is a diagrammatic illustration of the end of the imaging fiber bundle of FIG. 38 with an image from a first position.
Figure 40:
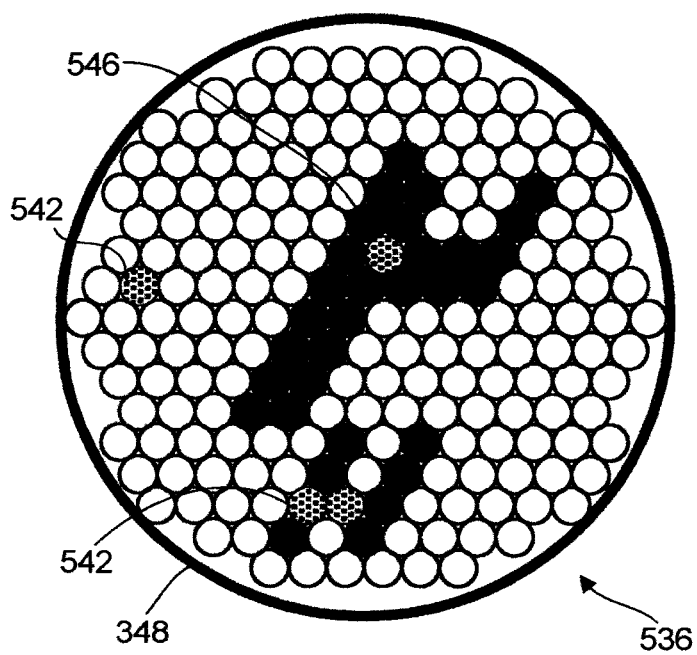
FIG. 40 is a diagrammatic illustration of the end of the imaging fiber bundle of FIG. 38 with an image from a second position.

Referring now to FIGS. 38 through 40, multiple sequential images can be used for image improvement. An image of a proximal end 536 of an imaging fiber bundle, such as imaging fiber bundle 348 in FIG. 35, can include normal, un-damaged fiber cores 540 and ambiguous imaging fiber cores 542 which can be dead fibers that are damaged and no longer guide light or which distort light, or have other problems. By gathering sequential images from different perspectives of the same features the dark or distorted areas can be resolved.

Referring to FIGS. 39 and 40 a first image view 544 and a second image view 546 are shown on proximal end 536 of imaging fiber bundle 538. First image view 544 can be from one perspective of distal end 500 of working assembly 304 (FIG. 22) and second image view 546 can be from a different perspective of distal end 500. Multiple sequential images can be generated from different perspective to improve an image because the distal end of the working assembly is typically in motion during use. This allows multiple images of the same features to be gathered from different perspectives (mostly different distances) and used by the imaging processor to create a more complete image than a single frame alone.

For example, in first image view 544 the ambiguous imaging fiber cores are located in one position with respect to the image and the ambiguous imaging fibers are located in another location, one pixel over to the left in second image view 546. Since the two different perspective use different imaging fiber cores at different times to convey the same pixel sized portion of the image, the imaging processor can determine which pixels, or imaging fiber cores are ambiguous and can use surrounding pixels to fill-in for the ambiguous fiber core. Such a technique can also be employed to remove any non-changing features of the image, e.g. the "chicken wire" described previously.

The foregoing descriptions of the invention have been presented for purposes of illustration and description. It is not intended to be exhaustive or to limit the invention to the precise form or forms disclosed, and other modifications and variations may be possible in light of the above teachings wherein those of skill in the art will recognize certain modifications, permutations, additions and sub-combinations thereof.

What is claimed is:

1. An endoscope working assembly, comprising:
    an imaging fiber bundle having a plurality of fiber cores, the fiber cores arranged to receive light at a distal end from a field of view and to transmit the light to a proximal end of the fiber cores and emit the light from the proximal end;
    an electronic imaging sensor, including multiple individual light sensing pixels, configured to produce electrical video signals in response to receiving the light, the imaging sensor optically coupled to the imaging fiber bundle to receive the light from the proximal end of the fiber cores with the fiber cores butt-coupled to the imaging sensor such that the image from each fiber core is received by at least one of the light sensing pixels;
    a working assembly connector fitting connected to the imaging fiber bundle and the electronic imaging sensor and configured to engage an imaging assembly connector fitting of an imaging assembly to removably attach the working assembly to the imaging assembly and arranged to electrically communicate the electrical video signals from the electronic imaging sensor to the imaging assembly; and
    an illumination arrangement including at least one illumination fiber extending from a proximal end at the working assembly connector fitting to a distal end substantially adjacent to the distal end of the imaging fiber bundle fiber cores, and at least one illumination source arranged to emit light that is optically coupled to the proximal end of the illumination fiber to transfer the emitted light through the illumination fiber to the distal end of the illumination fiber to illuminate the field of view, and the working assembly connector fitting is arranged to receive electrical energy from the imaging assembly connector fitting for powering the illumination source.

2. The endoscope working assembly of claim 1 wherein the imaging fiber bundle includes a diameter that is less than one millimeter.

3. The endoscope working assembly of claim 1 wherein each fiber core transfers light to a plurality of the light sensing pixels.

4. An endoscope, comprising:
    the working assembly of claim 1; and
    said imaging assembly including an imaging processor for use in producing imaging information including an image characteristic based on said light.

5. The endoscope of claim 4 wherein the imaging processor is configured to use the image characteristic for image correction.

6. The endoscope of claim 4 wherein the imaging processor is configured to use the image characteristic for spatial image correction.

7. The endoscope of claim 4 wherein the imaging processor is configured to use the image characteristic for stereoscopic imaging.

8. The endoscope of claim 4 wherein the imaging processor is configured to use the image characteristic for synthetic depth perception.

9. The endoscope of claim 4 wherein the imaging processor is configured to use the image characteristic for spectral analysis.

10. A method for producing an endoscope working assembly, said method comprising:
    providing an imaging fiber bundle having a plurality of fiber cores, the fiber cores arranged to receive light at a distal end from a field of view and to transmit the light to a proximal end of the fiber cores and emit the light from the proximal end;
    butt-coupling an electronic imaging sensor to the proximal end of the fiber cores to receive the light therefrom, the electronic imaging sensor including multiple individual light sensing pixels and configured to produce electrical video signals in response to receiving the light, such that the image from each fiber core is received by at least one of the light sensing pixels;
    connecting a working assembly connector fitting to the imaging fiber bundle and the electronic imaging sensor with the working assembly connector fitting configured to engage an imaging assembly connector fitting of an imaging assembly to removably attach the working assembly to the imaging assembly and arranged to electrically communicate the electrical video signals from the electronic imaging sensor to the imaging assembly; and
    configuring an illumination arrangement to include at least one illumination fiber extending from a proximal end at the working assembly connector fitting to a distal end substantially adjacent to the distal end of the imaging fiber bundle fiber cores, and at least one illumination source is arranged to emit light that is optically coupled to the proximal end of the illumination fiber to transfer the emitted light through the illumination fiber to the distal end of the illumination fiber to illuminate the field of view, and the working assembly connector fitting is arranged to receive electrical energy from the imaging assembly connector fitting for powering the illumination source.

* * * * *